US009678182B2

(12) United States Patent
Mandal et al.

(10) Patent No.: US 9,678,182 B2
(45) Date of Patent: Jun. 13, 2017

(54) SYSTEM AND METHOD FOR PROCESSING MAGNETIC RESONANCE SIGNALS

(71) Applicant: SCHLUMBERGER TECHNOLOGY CORPORATION, Sugar Land, TX (US)

(72) Inventors: Soumyajit Mandal, Cambridge, MA (US); Shin Utsuzawa, Missouri City, TX (US); Yi-Qiao Song, Newton Center, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 728 days.

(21) Appl. No.: 14/213,887

(22) Filed: Mar. 14, 2014

(65) Prior Publication Data

US 2015/0260813 A1 Sep. 17, 2015

(51) Int. Cl.
*G01R 33/46* (2006.01)
*G01V 3/34* (2006.01)
*G01R 33/36* (2006.01)
*G01V 3/14* (2006.01)
*G01V 3/32* (2006.01)
*G01N 24/08* (2006.01)

(52) U.S. Cl.
CPC ..... *G01R 33/3621* (2013.01); *G01R 33/3614* (2013.01); *G01V 3/32* (2013.01); *G01N 24/081* (2013.01)

(58) Field of Classification Search
CPC .. G01N 24/081; G01R 33/3621; G01R 33/28; G01R 33/3808; G01R 33/445; G01R 33/46; G01R 33/34; G01R 33/32; G01R 33/34092; G01R 33/36; G01R 33/3614; G01V 3/32

USPC .................................. 324/300–322
See application file for complete search history.

(56) References Cited

U.S. PATENT DOCUMENTS

| | | | |
|---|---|---|---|
| 4,975,644 A * | 12/1990 | Fox | G01R 33/3664 324/318 |
| 5,629,623 A | 5/1997 | Sezginer et al. | |
| 6,392,410 B2 | 5/2002 | Luong et al. | |
| 8,847,433 B2 * | 9/2014 | Vandermey | H01F 19/04 307/104 |
| 2012/0001629 A1 | 1/2012 | Hopper et al. | |
| 2013/0234705 A1 | 9/2013 | Mandal et al. | |
| 2013/0234706 A1 | 9/2013 | Mandal et al. | |

OTHER PUBLICATIONS

Hopper, et al., "Low-frequency NMR with a non-resonant circuit", Journal of Magnetic Resonance, vol. 210, Issue 1, May 2011, pp. 69-74.
Lepaisant, et al., "Low-noise preamplifier with input and feedback transformers for low source resistance sensors", Rev. Sci. Instr., vol. 63, pp. 2089-2094.
"Model SR554 Transformer Preamplifier", Stanford Research Systems Inc., Sunnyvale, California, 1999, 16 pages.

\* cited by examiner

*Primary Examiner* — Melissa Koval
*Assistant Examiner* — Rishi Patel

(57) ABSTRACT

A magnetic resonance (MR) receiver is described herein. The MR receiver can be used to process nuclear magnetic resonance (NMR) signals. The MR receiver includes a transformer that amplifies the MR signals and a preamplifier that receives the MR signals from the transformer. The preamplifier can include a transimpedance amplifier circuit with an input stage that includes a field effect transistor.

24 Claims, 15 Drawing Sheets

SYSTEM AND METHOD FOR PROCESSING MAGNETIC RESONANCE SIGNALS

TECHNICAL FIELD

This disclosure relates to magnetic resonance (MR) systems, and more particularly to MR receivers.

BACKGROUND

Magnetic resonance (MR) techniques can be used to determine properties of a substance. One example of a MR technique is a nuclear magnetic resonance (NMR) measurement. A NMR measurement typically includes applying a static magnetic field to the substance. The static magnetic field generates an initial magnetization of atomic nuclei within the substance. Then, an NMR system is used to apply an oscillating magnetic field at a particular frequency to the substance. The oscillating field is composed of a sequence of pulses that tip the magnetization of the atomic nuclei away from the initial magnetization. The pulse sequence can be arranged so that pulses and the static field interact with the nuclei to produce an NMR signal composed of "echoes" from within at least a portion of the substance. The NMR signal is detected and then used to determine NMR properties such as T1 relaxation time, T2 relaxation time, and attenuation of the signal due to molecular diffusion. These NMR properties can be used to determine the properties of the substance within the shell.

The portion of the substance where the NMR signal is generated is known as a "shell" or a "slice." "Non-resonant" NMR transmitters are able to apply pulse sequences at different frequencies to the substance and can investigate multiple shells within the substance in close temporal proximity. In turn, each shell produces an NMR signal at a different frequency. These signals can be received and then used to determine NMR properties of the shells.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to systems and methods for processing magnetic resonance (MR) signals, such as nuclear magnetic resonance (NMR) signals. In a specific embodiment, a NMR receiver is used to process NMR signals that are obtained from a substance. The NMR receiver includes a transformer that amplifies the NMR signal and a preamplifier for receiving the NMR signal from the transformer. The preamplifier includes a transimpedance amplifier circuit with an input stage that includes a field effect transistor. The transimpedance amplifier circuit provides a signal gain that is generally constant with frequency over a frequency band of interest. In some embodiments, the transimpedance amplifier circuit is followed by a differentiator circuit.

In another embodiment, the NMR receiver includes a transformer that amplifies the NMR signal and a preamplifier for receiving the NMR signal from the transformer. The preamplifier includes a transimpedance amplifier circuit that converts an input signal, which is proportional to current flowing from an NMR coil to the transformer, to an output signal in accordance with a defined transimpedance gain. The transimpedance amplifier circuit includes an operational amplifier circuit having a pair of input terminals and an output terminal. A feedback path is coupled between the output terminal and one input terminal of the operational amplifier. The feedback path includes an inductor configured such that the resultant signal produced by the transimpedance amplifier circuit has a voltage gain with respect to the input signal that is generally constant with frequency over a frequency band of interest.

Illustrative embodiments of the present disclosure are also directed to a method for processing a MR signal. The method includes receiving the MR signal and amplifying the MR signal using a transformer. The method further includes passing the MR signal produced by the transformer to a transimpedance amplifier circuit that includes an input stage with a field effect transistor. The method can further include passing the MR signal produced by the transimpedance amplifier circuit to a differentiator circuit for amplification.

BRIEF DESCRIPTION OF THE DRAWINGS

Those skilled in the art should more fully appreciate advantages of various embodiments of the disclosure from the following "Description of Illustrative Embodiments," discussed with reference to the drawings summarized immediately below.

DESCRIPTION OF ILLUSTRATIVE EMBODIMENTS

The term "generally constant with frequency" or "generally constant" as used herein to refer to voltage gain of an electrical signal over a range of frequencies means that the voltage gain of the electrical signal does not vary more than 3 dB over the range of frequencies.

Illustrative embodiments of the present disclosure are directed to systems and methods for processing magnetic resonance (MR) signals, such as nuclear magnetic resonance (NMR) signals. In a specific embodiment, an NMR receiver is used to process NMR signals that are obtained from a substance. The NMR receiver includes a transformer that amplifies the NMR signal and a preamplifier for receiving the NMR signal from the transformer. The preamplifier includes a transimpedance amplifier circuit followed by a differentiator circuit. The combination of the transimpedance amplifier circuit and the differentiator circuit provides a signal gain that is generally constant with frequency over a frequency band of interest. In one embodiment, the frequency band of interest lies with the frequency range between 50 KHz and 10 MHz and thus is suitable for desired NMR applications. The frequency band of interest can encompass the entire frequency range between 50 KHz and 10 MHz and thus can be suitable for a wide array of NMR applications. In another embodiment, the transimpedance amplifier circuit alone (without the differentiator circuit) provides a signal gain that is generally constant with frequency over the frequency band of interest. Using this configuration, various embodiments of the NMR receiver can receive and process NMR signals over the frequency band of interest, while also maintaining low noise. Furthermore, various embodiments of the NMR receiver can support "non-resonant" NMR transmitters, which produce resonant signal in multiple shells at different frequencies within the substance in close temporal proximity. Details of various embodiments are discussed below.

Figure 1:
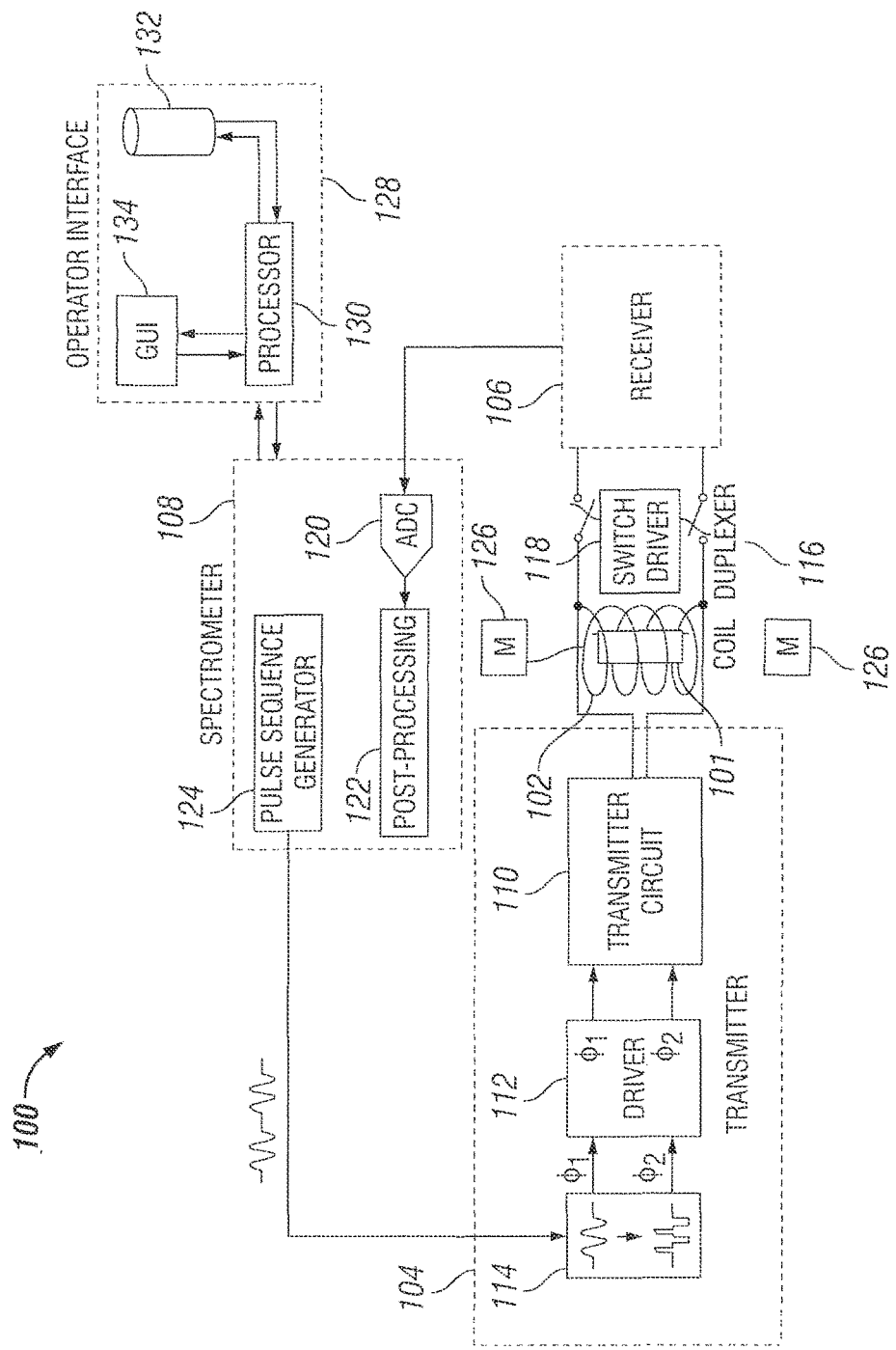
FIG. 1 shows a NMR system in accordance with one embodiment of the present disclosure.

FIG. 1 shows an NMR system 100 in accordance with one embodiment of the present disclosure. The NMR system 100 includes a coil 102 that is coupled to NMR electronics 104, 106, 108. A sample substance 101 is located inside and/or outside of the coil 102. The coil 102 applies NMR pulse sequences to the substance 101. The NMR electronics include a transmitter 104 and a receiver 106. Each of the transmitter 104 and the receiver 106 are coupled to the coil 102. In some embodiments, however, the NMR system 100 may include separate transmitter and receiver coils.

The NMR transmitter 104 includes a NMR transmitter circuit 110 that is coupled to the coil 102. The transmitter circuit 110 generates NMR pulse sequences and provides the NMR pulse sequences to the coil 102. The transmitter circuit 110 can be "non-resonant" because the resonant frequency of the circuit does not need to match the Larmor frequency of interest. In contrast, narrow-band circuits set their resonant frequencies to match the Larmor frequency of interest by selecting a particular capacitance for the transmitter circuit. Although the non-resonant transmitter circuit 110 and coil 102 may use capacitors and have some associated capacitance, this capacitance is not specifically selected to match a Larmor frequency of interest.

Illustrative embodiments of the NMR transmitter 104 described herein can switch between frequencies that are outside a natural resonant frequency bandwidth of a coil with a tuned circuit. In other words, the NMR transmitter does not depend on tuning a coil to set a particular frequency. In contrast to narrowband systems, which use mechanical switches and banks of fixed capacitors to tune the coil, various embodiments of the transmitters described herein achieve multi-frequency operation without a need for hardware modulation (e.g., switching between fixed capacitors or tuning between variable capacitors). Instead, the frequency can be modulated directly by a spectrometer. The NMR transmitter 104 is frequency insensitive and allows the pulse sequence frequency to be dynamically varied by the spectrometer while maintaining phase coherence of an output waveform. In some cases, the NMR transmitter 104 (and the coil 102) can switch between frequencies with a frequency difference as great as 10% of an initial applied frequency. In various other embodiments, the frequency can be even greater (e.g., 20% 30% or 50%). Also, in some embodiments, the NMR transmitter 104 can switch between frequencies in less than 5 µs. In yet further embodiments, the NMR transmitter 104 can switch between frequencies in less than 20 µs or 50 µs. Furthermore, in some embodiments, the NMR transmitter 104 can operate within a frequency range of 50 kHz to 10 MHz.

As shown in FIG. 1, the coil 102 is also coupled to a NMR receiver 106 so that NMR resonant signals that are generated within the substance 101 can be detected, amplified and analyzed. In one specific embodiment, the NMR receiver 106 is a broadband NMR receiver, which can receive and process resonant NMR signals over a frequency range of interest suitable for NMR applications. The coil 102 is coupled to the NMR receiver 106 using a duplexer 116. The duplexer 116 decouples the NMR receiver 106 from the coil 102 when the coil is operating in a transmitting mode (e.g., transmitting an NMR pulse sequence). In one particular embodiment, the duplexer 116 includes switches and a switch driver 118 that opens the switches during a transmitting mode and closes the switches during a receiving mode of operation. In this manner, the duplexer 116 protects the receiver 106 during a transmitting mode. A duplexer may not be used when the NMR system 100 includes separate transmit and receive coils.

The NMR system also includes a spectrometer 108 that is used to provide NMR pulse sequences to the NMR transmitter 104 and to analyze the NMR signal received from the NMR receiver 106. In various embodiments, the detected NMR signal is output by the NMR receiver 106 in analog form. In such embodiments, the spectrometer 108 may include a digitizer 120 (e.g., analog-to-digital converter) for converting the detected NMR signal into digital data. Furthermore, in various embodiments, demodulation of the NMR signal can occur within the spectrometer 108. In various other embodiments, however, demodulation of the NMR signal can also occur within the NMR receiver 106. The spectrometer 116 also includes a post-processor 122 that is used to interpret the detected digital NMR data and to determine NMR properties from the detected data. This data can be presented to a user using an operator interface with a graphical user interface (GUI). The spectrometer 108 also includes a pulse sequence generator 124 that generates NMR pulse sequences based upon parameters selected by an operator at the operator interface. The pulse sequence generator provides the sequences to the NMR transmitter 104. In one particular embodiment, the spectrometer 108 is a KEA™, which can be obtained from Magritek of Wellington, New Zealand. The spectrometer 108 can be controlled from the operator interface using PROSPA™ software, which can also be obtained from Magritek.

Further details of NMR electronics, NMR transmitters and NMR receivers are described in U.S. Publication No. 2012/0001629 published on Jan. 5, 2012 and U.S. application Ser. No. 13/774,457 filed on Feb. 22, 2013, each of which is incorporated by reference in their entireties.

As shown in FIG. 1, the NMR system 100 also includes a device 126 for applying a static magnetic field to the substance 101. In some embodiments, the device 126 is a magnet or an array of magnets. The magnets can be formed from a samarium-cobalt (SmCo) magnetic material.

The NMR system 100 also includes an operator interface 128 for communicating with the spectrometer 108. The operator interface 128 includes a computer system. The computer system may include a computer processor 130 (e.g., a microprocessor, microcontroller, digital signal processor, or general purpose computer) for executing any of the methods and processes described herein. The computer system may further include a memory 132 such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The memory 132 can be used to store computer instructions (e.g., computer program code) that are interpreted and executed by the processor 130.

NMR pulse sequences may be implemented as a series of computer instructions (e.g., software or firmware) fixed on a non-transitory tangible medium, such as a computer readable medium (e.g., a memory), or transmittable to the computer system, via a modem or other interface device, such as a communications adapter connected to a network over a tangible medium (e.g., optical or analog communications lines). The series of computer instructions can embody all or part of the NMR pulse sequences. The processor 130 may be configured to retrieve the sequences from the memory 132 and provide instructions to the NMR electronics 104, 106, 108 to apply the sequences to the substance 101. The detected resonant signals may also be communicated from the NMR electronics 104, 106, 108 to the processor 130 for storage on the memory 132.

The operator interface 128 also supports the graphical user interface 134 (GUI) (e.g., a monitor, a touch screen, a mouse, a keyboard and/or a joystick). The GUI 134 allows an operator to control and communicate with the NMR electronics 104, 106, 108. In various embodiments, the operator interface 128 can be used to perform functions selected from the following non-limiting list:

Communicate instructions to the NMR electronics 104, 106, 108 to initiate and/or terminate NMR measurements;

Communicate instructions to change parameters of NMR sequences to the NMR electronics (e.g., pulse amplitude of sequences, pulse lengths, timing between pulses, shape of pulses, and/or frequency of pulses);

Communicate detected NMR signal data from the NMR electronics 104, 106, 108 to the operator interface 128;

Communicate NMR pulse sequences from the operator interface 128 to the NMR electronics 104, 106, 108;

Perform analysis at the operator interface 128 of detected NMR signal data to determine NMR properties of substances;

Display various plots of NMR properties to the operator at the operator interface 128; and Communicate NMR pulse sequences from the operator interface 128 to the NMR electronics 104, 106, 108.

Illustrative embodiments of the present disclosure are not limited to the NMR system 100 shown in FIG. 1. Various modifications can be made to the system. For example, in one specific embodiment, the NMR electronics 104, 106, 108 include an additional computer system that supports the NMR electronics. In such an embodiment, the NMR electronics 104, 106, 108 and operator interface 128 may include their own communication modules, which provide for communication between the NMR electronics and the operator interface. A communications link between the communication modules can be established using, for example, a hard-wired link, an optical link, acoustic link, and/or a wireless link. By using the communication modules, the NMR electronics 104, 106, 108 and the operator interface 128 can be physically located in two separate locations. For example, in a wellbore application, the NMR electronics 104, 106, 108 can be located downhole, while the operator interface 128 is located at the surface.

Figure 2:
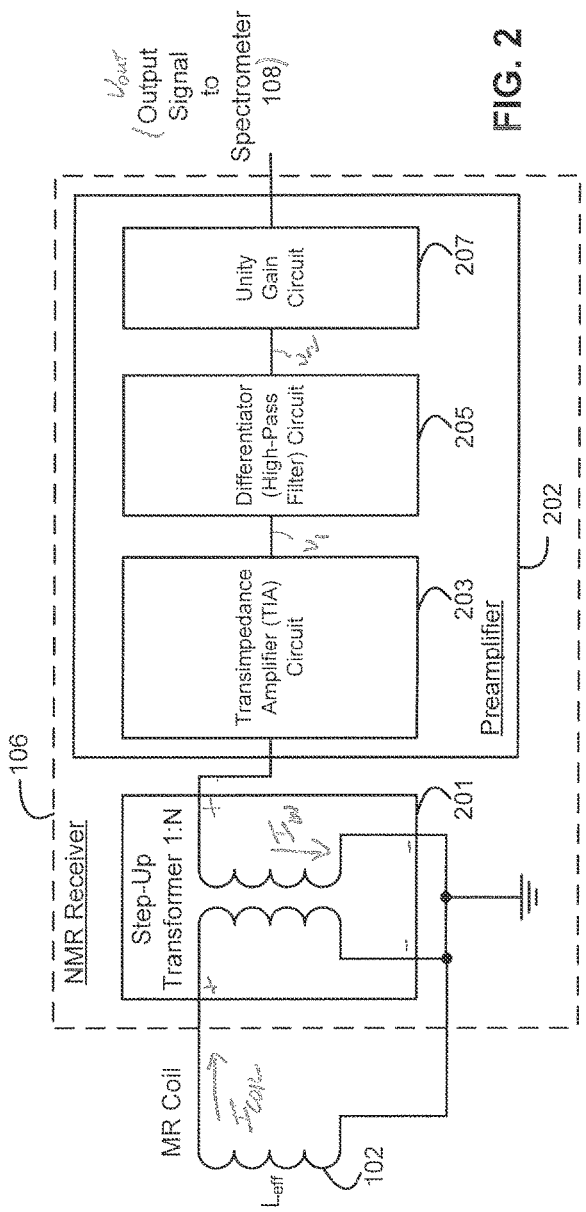
FIG. 2 shows a NMR receiver in accordance with one embodiment of the present disclosure.

Turning to FIG. 2, various embodiments of the NMR receiver 106 of FIG. 1 include a step-up transformer 201 and a preamplifier 202 that are operably coupled to the coil 102 and configured to process resonant NMR signals over a frequency band of interest. In one embodiment, the frequency band of interest lies within the frequency range between 50 KHz and 10 MHz and thus is suitable for desired NMR applications. The frequency band of interest can encompass the entire frequency range between 50 KHz and 10 MHz and thus can be suitable for a wide array of NMR applications. The preamplifier 202 includes a sequence of signal processing stages including a transimpedance amplifier (TIA) circuit 203, a differentiator circuit 205, and an optional unity gain circuit 207 as shown.

The step-up transformer 201 is a passive electrical device that transfers energy by inductive coupling between a primary winding and a secondary winding. The step-up transformer 201 provides voltage gain which is dictated by the turn ratio of its secondary winding relative to its primary winding. The turn ratio may be in the range of 1:2 to 1:10. However, in some embodiments, higher turn ratios can also be used. For certain applications (e.g., low frequency operation for NMR signals below 5 MHz), the step-up transformer 201 may include a magnetic core to increase the inductance and performance of the transformer 201. A magnetic shield may be installed around the transformer 201 in order to reduce the magnetic field projected from the magnet device 126 of the system into the transformer 201, which improves the performance of the transformer 201. For other applications, (e.g., higher frequency operation for NMR signals above 5 MHz), the transformer 201 may not use a magnetic core. The transformer 201 can provide for low insertion loss and a bandwidth that significantly exceeds the highest operating frequency of the NMR receiver 106. The voltage gain of the step-up transformer 201 is generally constant with frequency over the frequency band of interest. The step-up transformer 201 provides a low-noise voltage gain of the NMR signal that is detected at the coil 102. For example, the step-up transformer 201 can produce a low noise level at frequencies up to 10 MHz (e.g., 0.1 nV/Hz$^{1/2}$, which is equal to the thermal noise produced by a 0.6 Ohm resistor at 300 K). The amplified NMR signal produced at the output of the step-up transformer 201 is supplied to the TIA circuit 203 of the preamplifier circuit 200 for further amplification.

Figure 4:
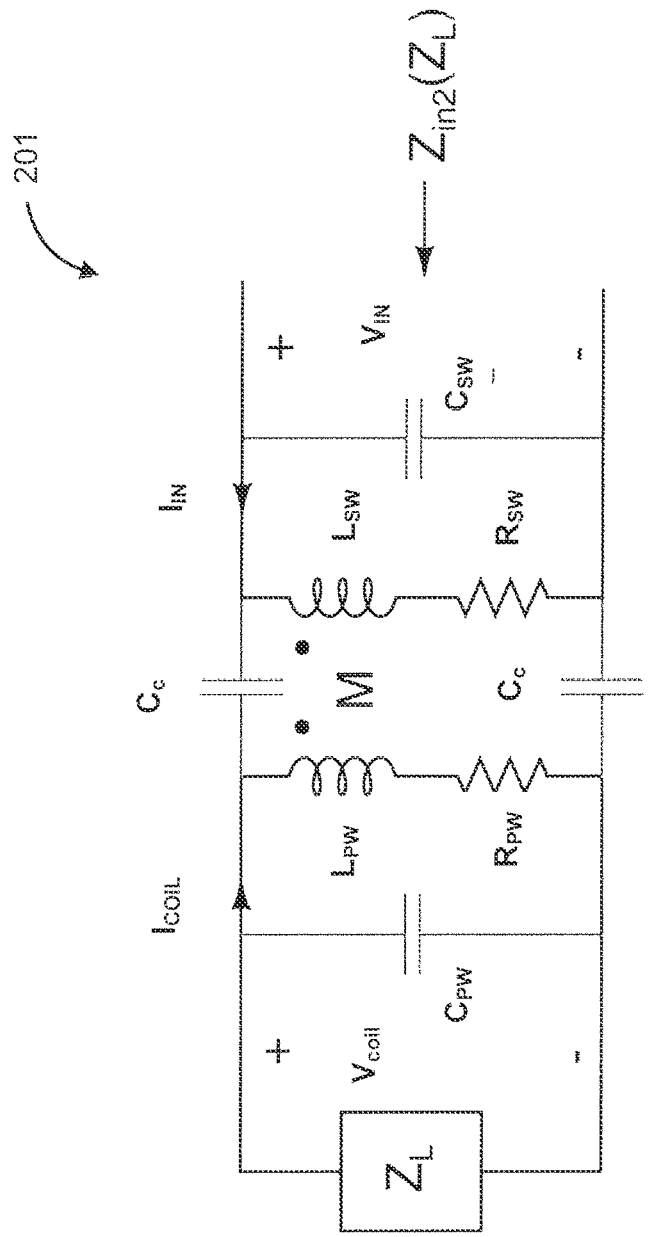
FIG. 4 is a schematic model of the step-up transformer of the NMR receiver of FIG. 2 in accordance with one embodiment of the present disclosure.

FIG. 4 illustrates an exemplary circuit model of the step-up transformer 201, including a series-coupled inductance $L_{PW}$ and resistance $R_{PW}$ of its primary winding as well as a series-coupled inductance $L_{SW}$ and resistance $R_{SW}$ of its secondary winding. The primary winding includes a parasitic intra-winding capacitance $C_{PW}$ coupled between the positive and negative terminals of the primary winding in parallel with the series-coupled inductance $L_{PW}$ and resistance $R_{PW}$ of the primary winding. The secondary winding includes a parasitic intra-winding capacitance $C_{SW}$ coupled between the positive and negative terminals of the secondary winding in parallel with the series-coupled inductance $L_{SW}$ and resistance $R_{SW}$ of the secondary winding. Parasitic inter-winding coupling capacitance $C_C$ is coupled between the positive terminal of primary winding and the positive terminal of the secondary winding, and parasitic inter-winding coupling capacitance $C_C$ is also coupled between the negative terminal of primary winding and the negative terminal of the secondary winding as shown. The positive and negative terminals of the primary winding are coupled to a load $Z_L$, which is provided by the coil 102 as evident from FIG. 2. The negative terminals of both the primary winding and the secondary winding of the step-up transformer 201 (as well as the negative terminal of the coil 102) are coupled to Ground potential as evident from FIG. 2. The positive terminal of the secondary winding of the step-up transformer 201 is coupled to the input of the TIA circuit 203 as evident from FIG. 2.

The step-up transformer 201 has a coupling constant k defined as:

$$k = \frac{M}{\sqrt{L_{PW}L_{SW}}}, 0 \leq k \leq 1, \quad (1)$$

where M is mutual inductance.

For an ideal transformer, k=1. However, for real transformers, k≤1. The input impedance of the step-up transformer 201, which is denoted $Zi_{n2}(Z_L)$ in FIG. 4, can be given as:

$$Z_{in2}(Z_L) \approx sL_{SW}(1-k^2) + R_{SW} + n_{eff}^2(R_{PW} + Z_L), \quad (2)$$

where $n_{eff} = \left(k^2 \frac{L_{SW}}{L_{PW}}\right)^{1/2} = kn$ \quad (3)

with $n = \sqrt{L_{SW}/L_{PW}}$ being the nominal turn ratio of the secondary winding relative to the primary winding. In this case, the input impedance $Zi_{n2}(Z_L)$ has three components. The first component, i.e., $sL_{SW}(1-k^2)$, is known as the leakage inductance. It quantifies the amount of magnetic flux that 'leaks' out of the transformer because of imperfect coupling between the windings, and it goes to zero as k→1. The second component, i.e., $R_{SW}$, is the series resistance of the secondary winding. The third component, i.e., $n_{eff}^2(R_{PW}+Z_L)$, is the impedance of the primary winding after the impedance transformation by $n_{eff}^2$. Here, $n_{eff}$ is the effective turn ratio of the step-up transformer 201 and is defined as the square root of the ratio by which the primary impedance gets transformed into the secondary size. It is also equal to the voltage gain of the step-up transformer 201.

For an ideal transformer, k=1 and $R_{PW}=R_{SW}=0$, which results in $Z_{in2}(Z_L)=n^2 Z_L$. In a real transformer, imperfect coupling reduces the reflected load impedance by a factor of $n_{eff}^2/n^2=k^2$, and the voltage gain by a factor of k. For the circuit of FIG. 2, the load $Z_L$ of the coil 102 can be expressed as:

$$Z_L = sL_{coil} + R_{coil}, \quad (4)$$

where $L_{coil}$ is the inductance of the coil 102, and $R_{coil}$ is the series resistance of the coil 102. The effective source impedance $Z_s$ of the step-up transformer 201 can be equated to the input impedance $Zi_{n2}(Z_L)$ given by the combination of Eqns. (2) and (4) and rewritten as follows:

$$Z_s = sL_{eff} + R_{eff} \quad (5)$$

where $$L_{eff} \approx L_{SW}(1-k^2) + n_{eff}^2 L_{coil}, \text{ and} \quad (6)$$

$$R_{eff} \approx R_{SW} + n_{eff}^2(R_{PW} + R_{coil}) \quad (7)$$

The effective source impedance $Z_S$ contributes to the voltage gain of the TIA circuit 203 of the preamplifier 200 as will be explained below.

Turning back to FIG. 2, the TIA circuit 203 of the preamplifier 200 receives the amplified NMR signal produced at the positive terminal output of the secondary winding of the step-up transformer 201, which is an input current signal $I_{IN}$ that is proportional to the current $I_{COIL}$ flowing through the coil 102 to the primary winding of the step-up transformer 201. The TIA circuit 203 operates to convert this input current signal ($I_{IN}$) to an output voltage signal ($V_1$) with transimpedance gain $R_T$ of ($V_1/I_{IN}$). The TIA circuit 203 can operate as an integrator (low-pass filter) that provides voltage gain that decreases with frequency over the frequency band of interest. In another embodiment, the circuit 203 can operate as a band-pass filter that filters out unwanted low frequency signal components while also providing voltage gain that decreases with frequency over the frequency band of interest.

Figure 3:
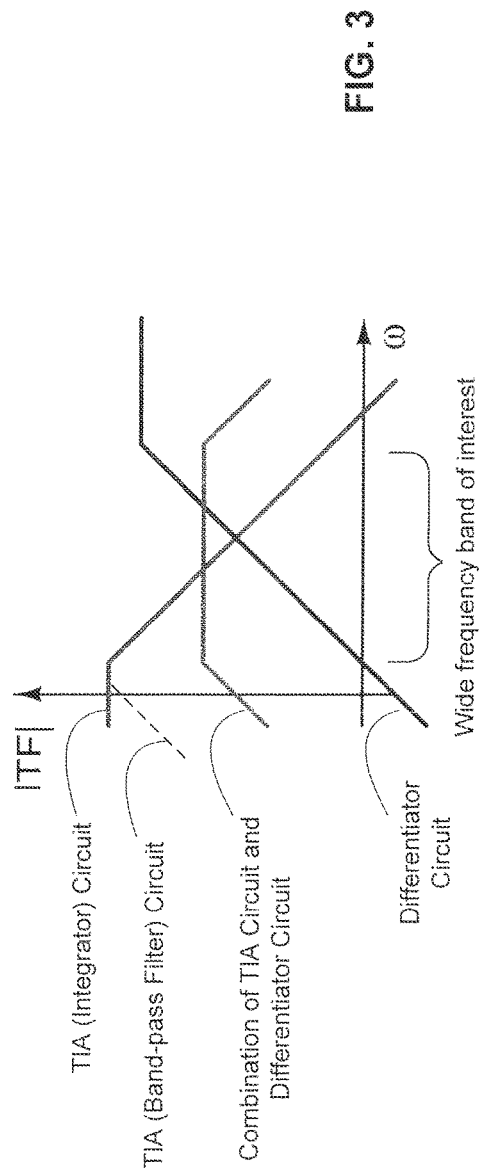
FIG. 3 is a Bode plot illustrating exemplary characteristics of the magnitude of the transfer function for different parts of the preamplifier circuit of the NMR receiver of FIG. 2 in accordance with one embodiment of the present disclosure.

The differentiator circuit 205 of the preamplifier 200 receives the amplified NMR signal produced at the output of the TIA circuit 203 and operates as a differentiator (high-pass filter) that produces a signal $V_2$ with voltage gain (relative to the signal $V_1$) that increases with frequency over the frequency band of interest. The combination of the circuit 203 and the circuit 205 provides a voltage gain that is generally constant with frequency over the frequency band of interest while performing bandpass filtering that filters out both low frequencies and high frequencies outside the frequency band of interest as illustrated schematically in the Bode plot of FIG. 3.

The unity gain circuit 207 receives the amplified NMR signal produced at the output of the differentiator circuit 205 and operates to produce an output signal $V_{OUT}$ with minimal voltage gain (relative to the signal $V_2$) over the frequency band of interest. The unity gain circuit 207 can be designed to be stable while driving large capacitive loads, such as long lengths of coaxial cable. This design ensures that the NMR receiver 106 can be located away from the spectrometer 108, if necessary.

Figure 5:
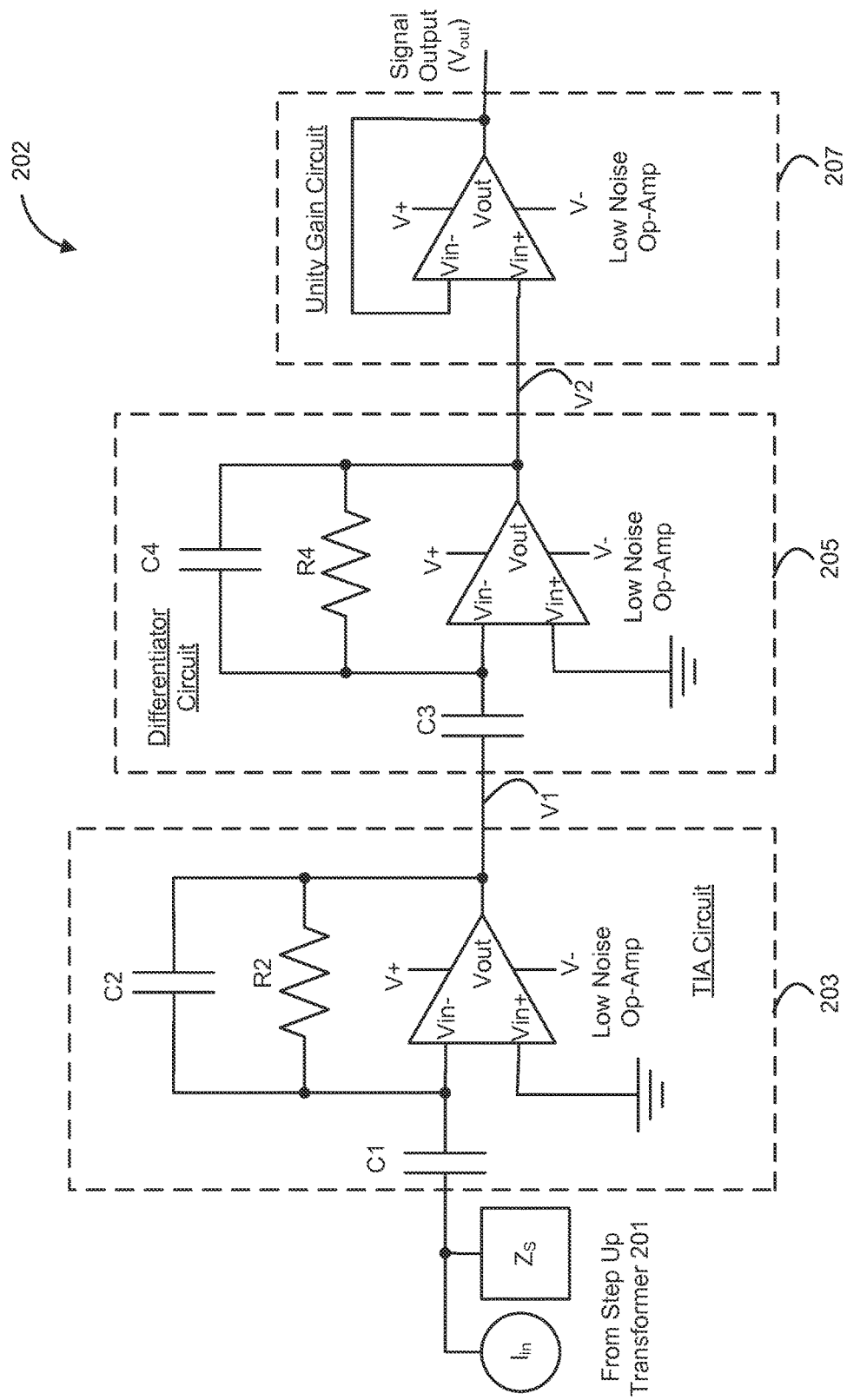
FIG. 5 shows an exemplary preamplifier circuit that is part of the NMR receiver of FIG. 2 in accordance with one embodiment of the present disclosure.

In one embodiment illustrated in FIG. 5, the TIA circuit 203 of the preamplifier 202 can be realized by a low-noise operational amplifier 501 configured as a transimpedance (or current-sense) amplifier stage. In this configuration, the positive input terminal (Vin+) of the operational amplifier 501 is coupled to Ground potential. A feedback path between the output terminal (Vout) of the operational amplifier 501 and its negative input terminal (Vin−) includes a resistor R2 that sets the transimpedance gain of the TIA circuit 203. Specifically, the transimpedance gain $R_T$ of the TIA circuit 203 can be given as:

$$R_T = Z_2/I_{IN}, \quad (8)$$

The current source ($I_{in}$) and the effective parallel source impedance ($Z_s$) that represents the step-up transformer 201 can be converted to an equivalent voltage source $v_{in}$ of $I_{in}*Z_S$ and a series impedance $Z_S$ (e.g., Norton to Thevenin conversion) to provide a voltage gain of:

$$\frac{V_{out}}{V_{in}} = \frac{Z_2}{Z_s}. \quad (9)$$

Figure 6:
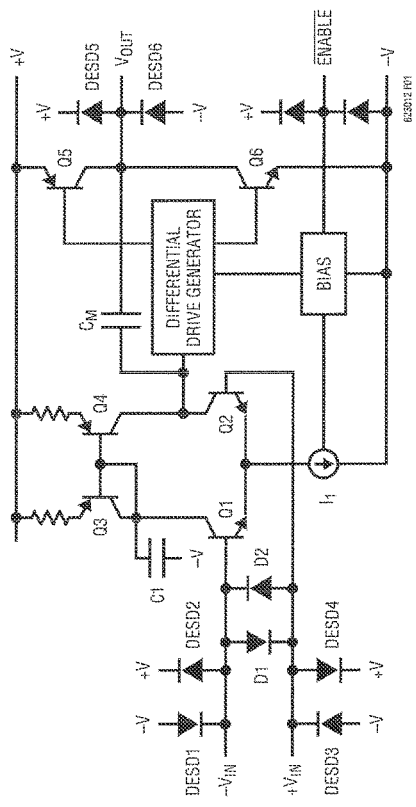
FIG. 6 shows a schematic of an operational amplifier circuit that can be used as part of the preamplifier circuit of FIG. 5 in accordance with one embodiment of the present disclosure.

The operational amplifier 501 can be decompensated. For example, the operational amplifier 501 can be a decompensated version of the LT6230 family operational amplifier (specifically, the LT6230-10 operational amplifier) sold commercially by Linear Technology Corp. of Milpitas, Calif. FIG. 6 is a schematic diagram of the circuitry embodied by the LT6230 family of operational amplifiers. The LT6230 family of operational amplifiers has BJT inputs that are protected with diode clamps, internal dominant-pole compensation, common-source output stages, and a compensation capacitor $C_M$ that ensures that the amplifier is unity-gain stable, but limits its bandwidth. However, the LT6230 family of operational amplifiers is sold in decompensated versions where the compensation capacitor $C_M$ has been reduced. These versions are no longer unity-gain stable (for example, the LT6230-10 is only stable for gains greater than 10), but have much more bandwidth. For the case where the operational amplifier 501 is decompensated, the feedback path between the output terminal (Vout) and the negative input terminal (Vin−) of the operational amplifier 501 can include an additional compensation capacitor C2 coupled in parallel with the resistor R2 as shown. The compensation capacitor C2 reduces the gain of the TIA circuit 203 at high frequencies in order to ensure that it remains stable. The circuit 203 can also include a capacitor C1 coupled in series between the output of the step-up transformer 201 and the negative input terminal (Vin−) of the operational amplifier 501 as shown. This series-coupled capacitor C1 increases the source impedance $Z_s$ of the step-up transformer 201 at low frequencies such that the source impedance $Z_s$ is represented as:

$$Z_s = sL_{eff} + R_{eff} + \frac{1}{sC_1}. \quad (10)$$

As a result, the TIA circuit 203 operates as a band-pass filter, rather than a pure integrator or low-pass filter. In this case, the low frequency filtering of the band-pass filter operations eliminates low frequency offsets, drift and capacitive pickup, and the TIA circuit 203 has a voltage gain ($v_1/v_{in}$) given by:

$$v_1 v_{in} = \frac{R_2}{Z_s} = \frac{R_2}{sL_{eff} + R_{eff} + \frac{1}{sC_1}} \quad (11)$$

$$= \frac{R_2}{R_{eff}} \left( \frac{s\tau_0/Q}{s^2\tau_0^2 + s\tau_0/Q + 1} \right) \quad (12)$$

where $$\tau_0 = \sqrt{L_{eff} C_1}, \quad Q = \frac{\sqrt{L_{eff} C_1}}{R_{eff}} \quad (13)$$

Here $1/\tau_0$ and Q are the center frequency and quality factor, respectively, of the bandpass filter operations of the TIA circuit 203. The value of the capacitor C1 can be large enough to ensure that Q is small and there in not much peaking in the overall response around the center frequency $1/\tau_0$. Note that the voltage gain of the TIA circuit 203 does not depend on the inductance $L_{PW}$ of the primary winding of the step-up transformer 201 as long as $L_{eff} \approx L_{coil}$, i.e., $L_{coil} \gg L_{PW}(1-k^2)$. This constraint ensures that the input current $I_{IN}$ sensed by the TIA circuit 203, which is proportional to the current flowing through the coil 102 to the primary winding of the step-up transformer 201, is not reduced by the leakage inductance of the step-up transformer 201. Note that the capacitor C1 can be omitted. In this case, the TIA circuit 203 operates as pure integrator (low-pass filter).

In one embodiment as shown in FIG. 5, the differentiator circuit 205 of the preamplifier 202 includes a low-noise operational amplifier 503 whose positive input terminal (Vin+) is coupled to Ground potential. The feedback path between the output terminal (Vout) of the operational amplifier 503 and its negative input terminal (Vin−) includes a resistor R4 and a capacitor C4 coupled in parallel with respect to one another. The differentiator circuit 205 can also include a capacitor C3 coupled in series between the output of the circuit 203 and the negative input terminal (Vin−) of the operational amplifier 503 as shown. The operational amplifier 503 can be internally compensated and thus need not require external compensation. For example, the operational amplifier 503 can be an internally compensated version of the LT6230 family operational amplifier (specifically, the LT6230 operational amplifier) sold commercially by Linear Technology Corp. of Milpitas, Calif. The differentiator circuit 205 of FIG. 5 has a voltage gain ($v_2/v_1$) given by:

$$v_2/v_1 = \frac{-sC_3}{sC_4 + \frac{1}{R_4}} = -A_2\left(\frac{s\tau_2}{s\tau_2 + 1}\right), \quad (14)$$

where $$\tau_2 = R_4 C_4, \quad A_2 = \frac{C_3}{C_4} \quad (15)$$

The unity gain circuit 207 can be realized by a low-noise operational amplifier 505 whose positive input terminal (Vin+) is coupled to the output of the differentiator circuit 205. A feedback path with minimal resistance is coupled between the output terminal (Vout) of the operational amplifier 505 and its negative input terminal (Vin−). This topology provides unity voltage gain between the positive input terminal (Vin+) and the output terminal (Vout) of the operational amplifier 505 to provide:

$$v_{out} = v_2. \quad (16)$$

The operational amplifier 505 also is capable of driving large capacitive loads at its output terminal (Vout). The operational amplifier 505 can be realized by the LT1363 operational amplifier sold commercially by Linear Technology Corp. of Milpitas, Calif.

The combination of the TIA circuit 203, the differentiator circuit 205, and the unity gain circuit 207 of FIG. 5 provides a voltage gain given by the combination of Eqns. (12), (14) and (16) as follows:

$$v_{out}/v_{in} = (v_1/v_{in})(v_2/v_1)(v_{out}/v_2), \quad (17)$$

$$= \left(\frac{R_2}{R_{eff}}\left(\frac{s\tau_0/Q}{s^2\tau_0^2 + s\tau_0/Q + 1}\right)\right)\left(-A_2\left(\frac{s\tau_2}{s\tau_2 + 1}\right)\right)(1) \quad (18)$$

The voltage gain is generally constant at a value of $A_2 \tau_2/\tau_0$ for a frequency range that extends from $1/\tau_0$ to $1/\tau_2$. In one embodiment, the components of the TIA circuit 203 and the differentiator circuit 205 are selected such that the frequency range that extends from $1/\tau_0$ to $1/\tau_2$ encompasses a frequency band of interest suitable for NMR applications (for example, from 50 KHz to 10 MHz).

In illustrative embodiments, an advantage of the transimpedance amplifier configuration of circuit 203 is that it is robust to disturbances (such as capacitive pickup) at the input, or sense terminal. This robustness is due to active feedback, which is used to reduce the impedance at the input terminal. The voltage gain of the transimpedance amplifier configuration of circuit 203 is set by the feedback resistance R2 and the source impedance $Z_s$, which is represented as $$Z_s = sL_{eff} + R_{eff} + \frac{1}{sC_1}.$$

In the system, the source impedance $Z_s$ is predominantly inductive. As illustrated in the embodiment described below with respect to FIG. 14, an inductive feedback element can be used in order to provide generally constant voltage gain over a range of frequencies. However, in order to ensure large enough gain, the inductive feedback element is much larger than the source impedance and in many cases the feedback inductance becomes inconveniently large. This issue is avoided using resistive feedback (feedback resistance R2) with a tradeoff that the TIA circuit 203 behaves as a band-pass filter with gain that decreases with frequency. The noise of the feedback resistance R2 can be neglected as long as its value is large enough to ensure high gain at all frequencies of interest.

Figure 7:
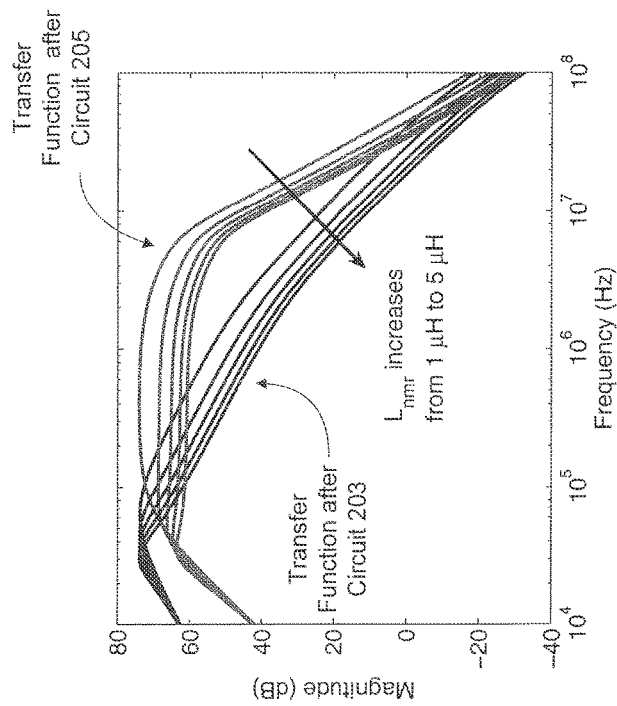
FIG. 7 is a Bode plot derived from simulation of the NMR receiver of FIG. 2 illustrating exemplary characteristics of the magnitude of the transfer function for different parts of the preamplifier circuit of FIG. 5 for a number of coils of varying inductance.

The operational characteristics of NMR receiver circuitry embodied by the step-up transformer 201 of FIG. 4 together with the preamplifier 202 of FIG. 5 can be simulated with the following parameters. The step-up transformer 201 has a turn ratio n of 6, a k of 0.9999, an inductance $L_{PW}$ of its primary winding of 239 µH, an inductance $L_{SW}$ of its secondary winding of 8.6 mH, a resistance $R_{PW}$ of its primary winding of 0.2 Ohms, a resistance $R_{SW}$ of its secondary winding of 1.2 Ohms, and parasitic capacitances $C_{PW}$, $C_{SW}$, $C_C$ all equal to 3 pF. Other circuit parameters include the compensation capacitor C2 of the TIA circuit 203 having a capacitance of 1.5 pF, the feedback resistor R2 of the TIA circuit 203 having a resistance of 20 Kohms, the capacitor C1 of the TIA circuit 203 having a capacitance of 0.2 µF, the feedback capacitor C4 of the differentiator circuit 205 having a capacitance of 50 pF, the feedback resistor R4 of the differentiator circuit 205 having a resistance of 1 KOhms, and the capacitor C3 of the differentiator circuit 205 having a capacitance of 1.5 nF. FIG. 7 shows the magnitude of the simulated transfer function after the TIA circuit 203 of FIG. 5 and after the combination of the TIA circuit 203 of FIG. 4 and the differentiator circuit 205 of FIG. 5 for different values of the coil inductance (referred to as $L_{coil}$ or $L_{nmr}$). Note that TIA circuit 203 of FIG. 5 behaves as a bandpass filter, while the voltage gain after differentiator circuit 205 of FIG. 5 is generally constant over approximately two decades in frequency from 50 kHz to 5 MHz.

Figure 8B:
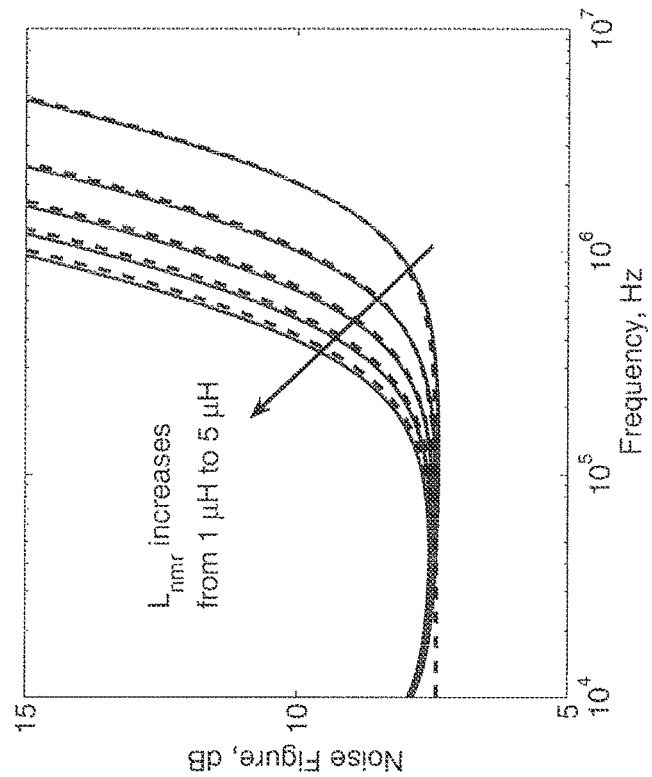
FIG. 8B shows both the simulated noise figure (NF) (in solid lines) and theoretical predictions of the NF (in dashed lines) of the NMR receiver of FIG. 2 for a number of coils of varying inductance, where the NMR receiver of FIG. 2 employs the preamplifier circuit of FIG. 5.
Figure 8A:
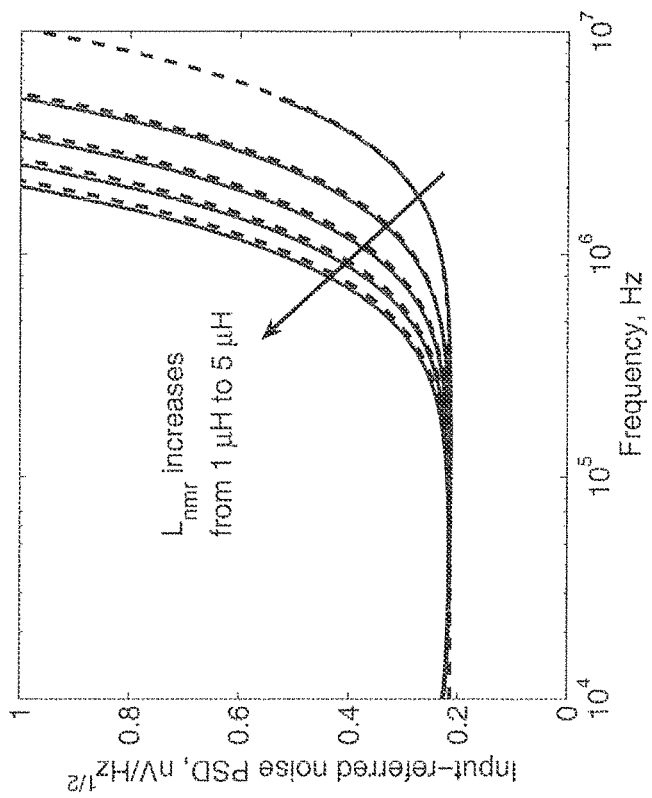
FIG. 8A shows both the simulated input-referred noise power spectral density (PSD) (in solid lines) and theoretical predictions of the input-referred noise PSD (in dashed lines) of the NMR receiver of FIG. 2 for a number of coils of varying inductance, where the NMR receiver of FIG. 2 employs the preamplifier circuit of FIG. 5.

FIG. 8A shows the simulated input-referred noise power spectral density (PSD) of such NMR receiver circuitry as well as input-referred noise power spectral density (PSD) of such NMR receiver circuitry predicted by the following:

$$v_{ni}^2 = v_{ns}^2 + e_n^2 + [(Z_1 \| Z_2)^2 + |Z_s|^2] i_n^2, \quad (19)$$

where $v_{ns}^2$ is the noise power spectral density of the source, $e_n$ is the noise voltage source, $i_n$ is the noise current source, and $Z_2/Z_1$ is the gain set by the negative feedback of operational amplifier 501. The input-referred noise power spectral density (PSD) of the simulations are shown as solid lines, while theoretical predictions of the input-referred noise power spectral density (PSD) are shown as dashed lines. The simulations and the theory are in good agreement with each other. Note that the step-up transformer 201 reduces the low-frequency input-referred noise PSD of the NMR receiver circuitry to the very low value of 0.23 nV/Hz$^{1/2}$, which is equal to that of a 3.3 Ohm resistor at 300 K. In this region of low-frequency operation, voltage noise is dominant. The input-referred noise PSD of the NMR receiver circuitry increases sharply at high frequencies because of current noise. The amount of current noise increases with larger coil inductance. This is because the source impedance is approximately proportional to the coil inductance.

FIG. 8B shows the simulated noise figure (NF) of such NMR circuitry as well as the NF of such NMR receiver circuitry predicted by the following:

$$NF = 1 + \left[\frac{R_{pw}}{R_{coil}}\left(1 + \frac{1}{n}\right)\right] + \left[\frac{R_e}{n^2 R_{coil}}\left[1 + \left(\frac{Q_s R_{eff}}{R_n}\right)^2\right]\right], \quad (20)$$

where $R_e$ is input-references noise resistance of the operational amplifier 501 of FIG. 5, $Q_s$ is the quality factor of the source impedance $Z_s$, and $R_n=e_n/i_n$ is the optimal source resistance for minimizing NF, i.e., for noise matching. The first term in the expression for NF is equal to 1. It corresponds to noise contributed by the input NMR signal. The second term corresponds to noise added by the step-up transformer 201. The third term corresponds to the noise added by the operational amplifier 501 of the TIA circuit 203 of FIG. 5. In deriving this expression, it is assumed that the primary and secondary windings of the step-up transformer 201 use the same wire, so that $R_{SW}\approx nR_{PW}$. Within the second term, the first sub-term is contributed by the primary winding of the transformer 201, while the second sub-term is contributed by the secondary winding of the transformer 201. The second sub-term can be neglected if n>>1. This behavior occurs because the ratio of signal voltages across the transformer is a n, but the ratio of noise voltages contributed by the windings is $\propto\sqrt{R_{SW}/R_{PW}}=\sqrt{n}$. The third term consists of two sub-terms. The first sub-term is due to the voltage noise of the operational amplifier 501 of the TIA circuit 203 of FIG. 5, while the second sub-term is due to the current noise of the operational amplifier 501 of the TIA circuit 203 of FIG. 5. The effects of current noise increase rapidly at high frequencies and for large values of $L_{eff}$ which result in large Q. In addition, current noise is important for large source resistances, i.e., when $R_{eff}$ is large. This equation provides for prediction of NF for a given coil and transformer. The NFs of the simulations are shown as solid lines, while theoretical predictions of the NF are shown as dashed lines. The simulations and the theory are again in good agreement with each other.

Figure 9:
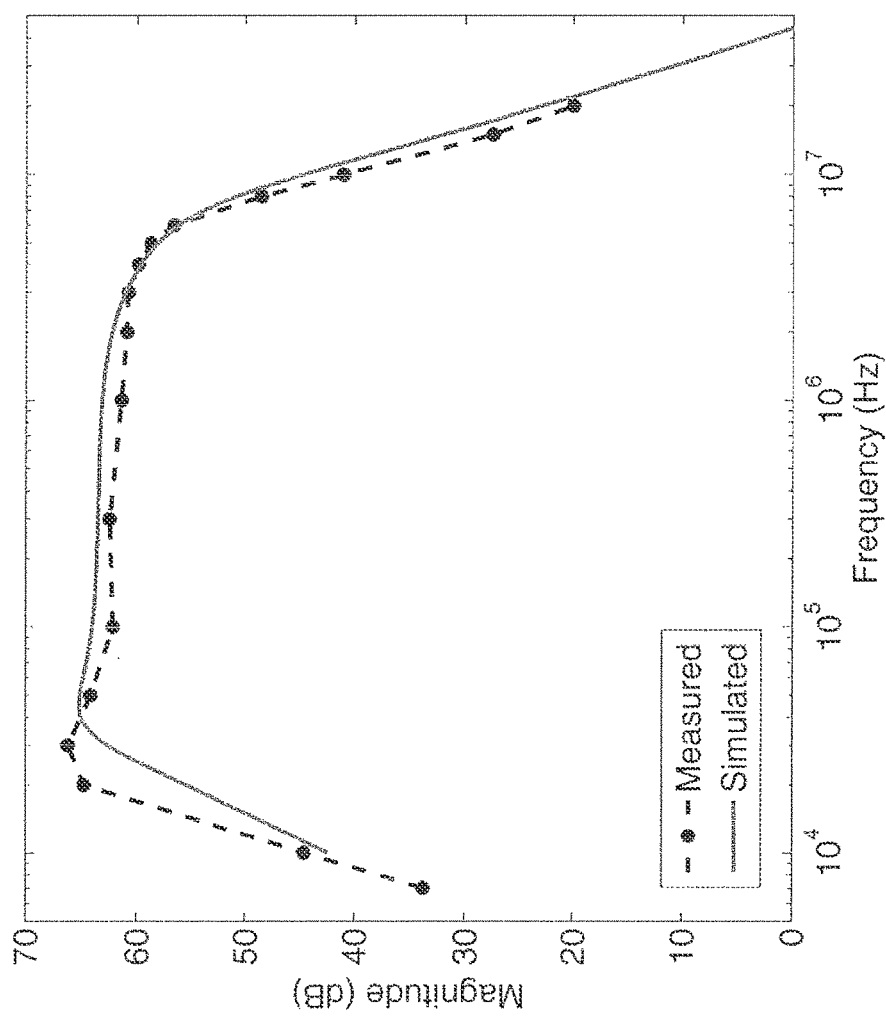
FIG. 9 shows both the measured gain (in a dashed line) and the simulated gain (in a solid line) of a prototype NMR receiver circuit for a coil with an inductance of 3.8 µH.

The circuit simulations of FIGS. 7, 8A, and 8B can be verified by prototyping the simulated NMR receiver circuit on a printed circuit board and testing the prototype NMR receiver circuit. FIG. 9 shows both the magnitude of measured and simulated voltage gain of the prototype NMR receiver circuit over a wide range of frequencies for a coil with an inductance of 3.8 µH. In order to make these measurements, small-amplitude sinusoidal signals can be fed into the coil through a weakly-coupled secondary coil that was driven by a function generator. Weak coupling ensured that the secondary coil did not significantly affect the voltage transfer function of the prototype NMR receiver circuit. Note that the magnitude of the measured and simulated voltage gains match each other very well over the range of frequencies, which validates the circuit simulations of FIGS. 7, 8A and 8B.

Figure 10:
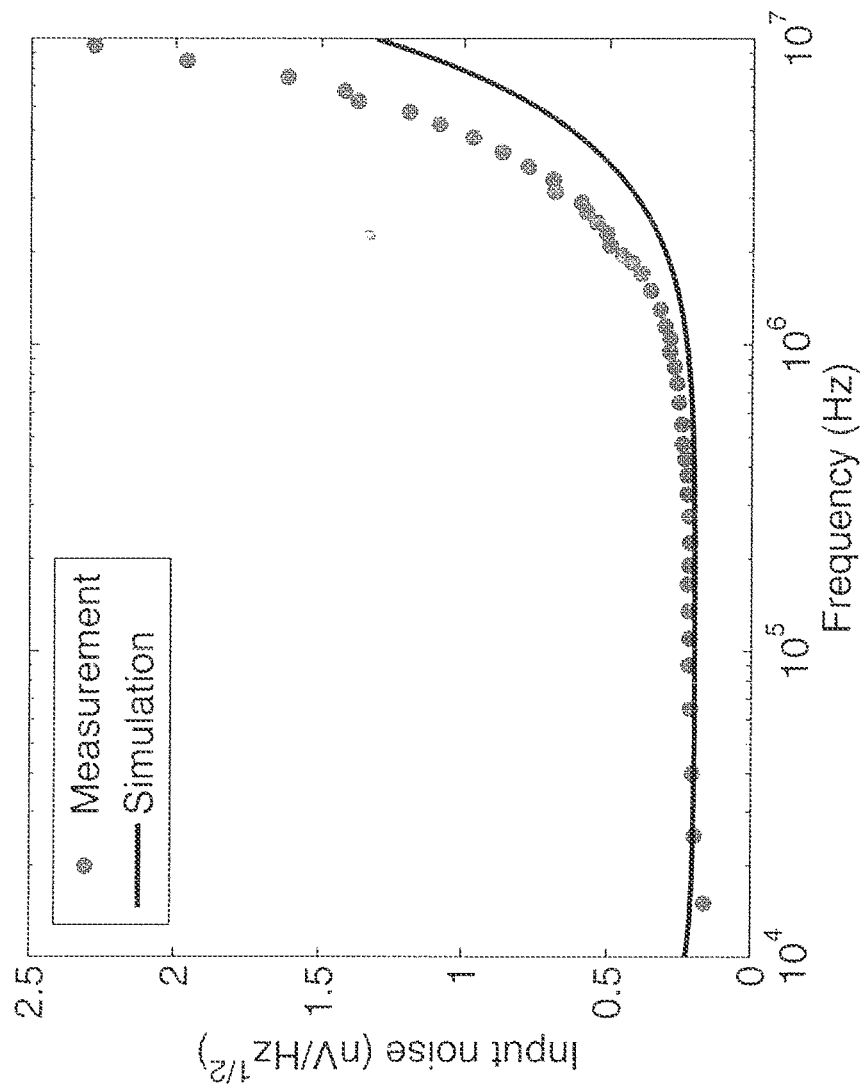
FIG. 10 shows both the measured input-referred noise power spectral density (PSD) (in dots) and simulated input-referred noise PSD (in a solid line) of the prototype NMR receiver circuit of FIG. 9, which employed a coil with an inductance of 3.8 µH.

The input-referred noise of the prototype NMR receiver circuit can be measured through the use of a carefully-shielded dummy coil as the load. The center conductor of a short length of coaxial cable can be removed and replaced with a small inductor containing a ferrite core, resulting in a coil inductance of 1.35 µH and a coil resistance of 0.75 Ohms. The output noise of the prototype NMR receiver circuit can be measured with a spectrum analyzer (e.g., 4395A Network/Spectrum/Impedance Analyzer sold by Agilent of Santa Clara, Calif.) by shorting one end of the coil and connecting the other end to the input. The short end of the coil can be removed and replaced with a specially-built resistive attenuator (74 dB attenuation, 50 Ohm input impedance, 1 Ohm output impedance). A function generator can be used to feed a sinusoidal signal into the attenuator, and the spectrum analyzer can be used to measure the amplitude of the output signal. The input amplitude can be kept low enough to ensure that the operation of the prototype NMR receiver circuit remains linear. The frequency of the sinusoidal signal can then be varied, and the small-signal gain calculated at each point. Finally, the measured output noise can be divided by the measured gain to obtain the input-referred noise as a function of frequency. FIG. 10 shows the measured input-referred noise of the prototype NMR receiver circuit. The expected noise level based on circuit simulations is also shown as a solid line for comparison. The two curves match very well up to about 2 MHz, but there is somewhat more noise than expected at higher frequencies. This excess noise may be due to core loss in the transformer, higher-than-expected current noise in the TIA circuit 203, or noise injected by the DC power supply. In order to eliminate power supply noise, the experiment was re-run after replacing the bench-top power supply with batteries (4 C-type alkaline cells connected in series to generate 6V). There were no significant differences in performance, proving that the effects of power supply noise are negligible. Overall, the transformer-coupling strategy performs very well. For example, the measured input-referred noise at 1 MHz is 0.29 nV/Hz$^{1/2}$, which is equivalent to a 5.2 Ohm resistor. This value is 3.8 times lower than the voltage noise of the LT6230 operational amplifier alone (1.1 nV/Hz$^{1/2}$).

Figure 11A:
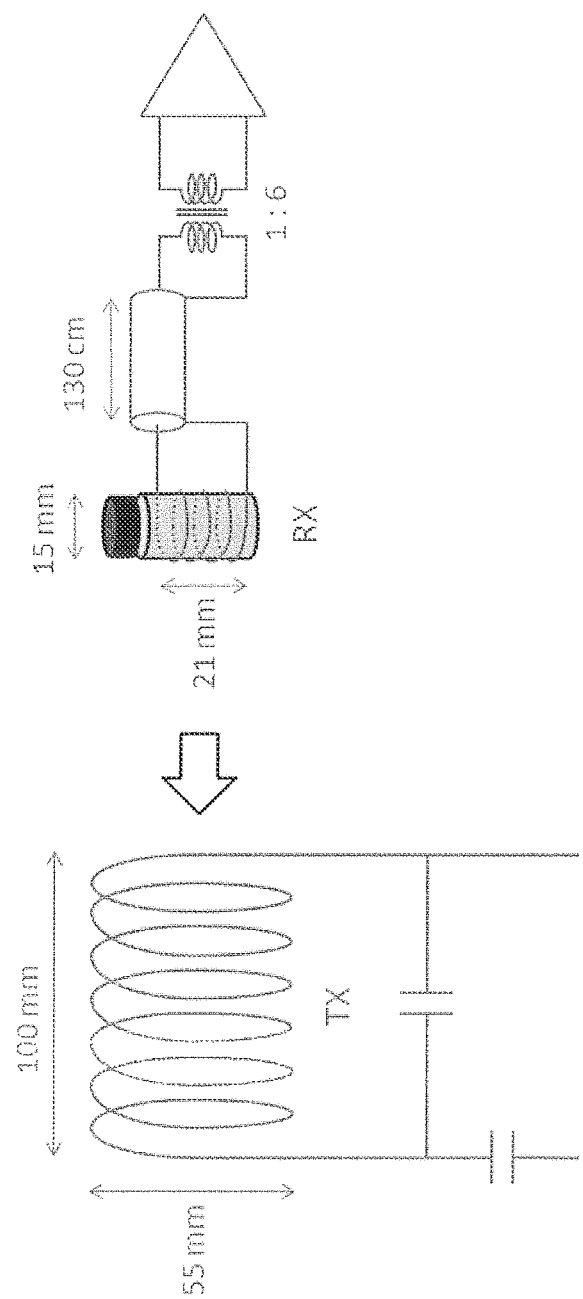
FIG. 11A is a schematic of a proof-of-concept experimental setup that utilizes the prototype NMR receiver circuit of FIG. 9.

The prototype NMR receiver circuit was also used to detect proton NMR signals in the fringe field of a 2T superconducting magnet. The Larmor frequency at a chosen location was $f_0$=2.0 MHz. The proof-of-concept experimental setup is shown in FIG. 11A. In this setup, an untuned receive coil was accommodated inside a tuned, perpendicular transmit coil, and interfaced with the prototype NMR receiver circuit. To form the receive coil, twelve turns of copper wire were wound on a vial containing doped water. The impedance of the receive coil was $Z_C$=0.2+j18 Ohms at 2 MHz, corresponding to an inductance $L_{coil}$ of 1.4 µH. When the transmit coil was tuned to 2 MHz, isolation between the transmit coil and the receive coil was 34 dB. The receive coil was coupled to the prototype NMR receiver circuit. The output of the prototype NMR receiver circuit was fed into a commercial spectrometer (Kea™, Magritek) for further amplification and digitization. A CPMG sequence with 40 µs long π-pulses provided a slice of a few millimeters in the gradient field, and signal bandwidth was limited by the excitation bandwidth.

Figure 11B:
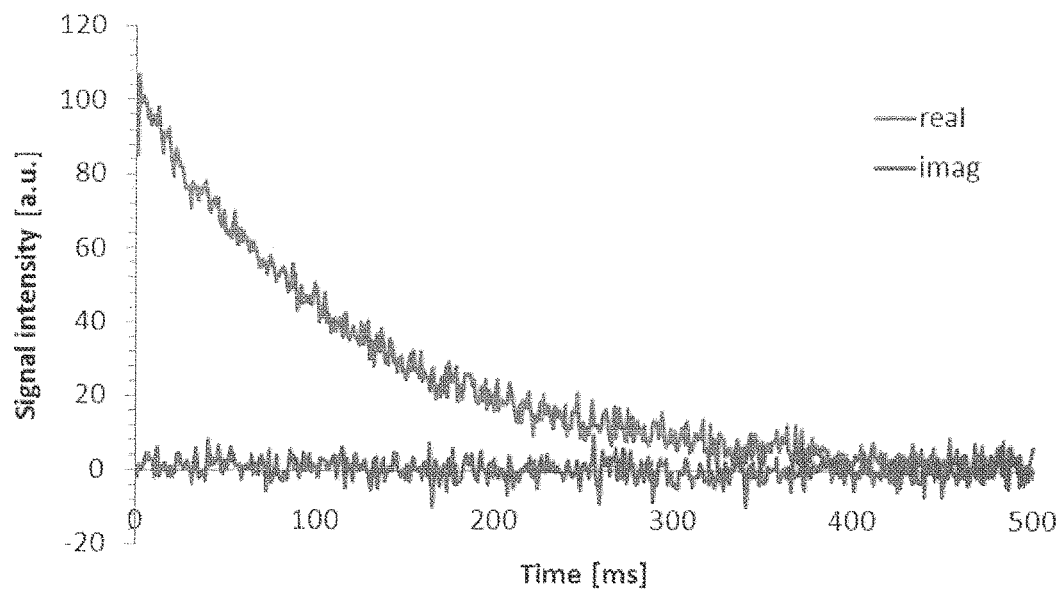
FIG. 11B shows the CPMG signal obtained with the prototype NMR receiver circuit as part of the experimental setup of FIG. 11A with the receive coil having an inductance of 1.4 µH.

FIG. 11B shows the CPMG signal obtained with the prototype NMR receiver circuit with the receive coil having an inductance $L_{coil}$ of 1.4 µH. The initial signal-to-noise ratio after 512 averages was 36.

Another set of experiments were performed with a receive coil that had approximately double the number of turns (22 versus 12), but the same total length. This receive coil had an inductance $L_{coil}$ of 4.1 µH.

Figure 11C:
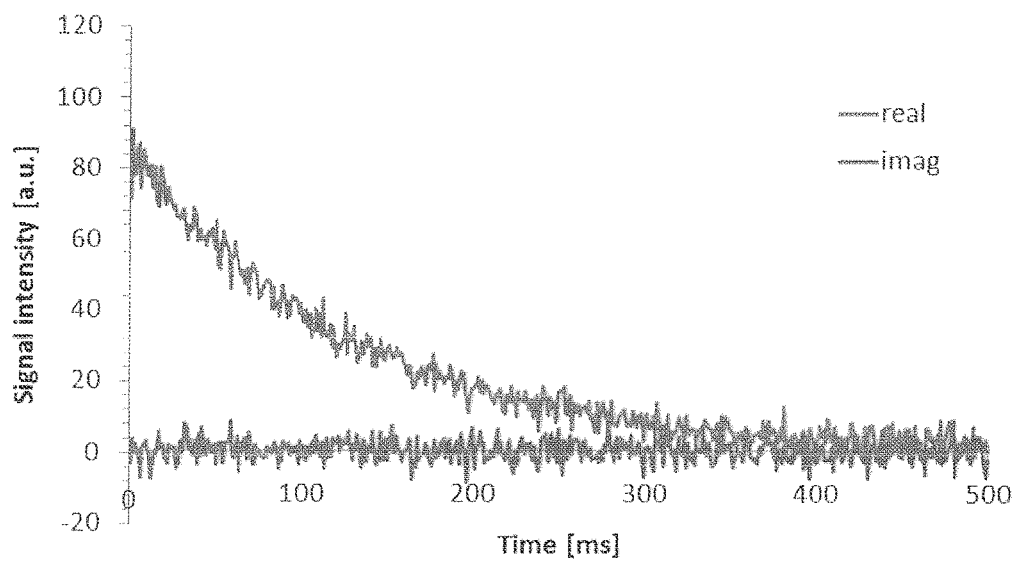
FIG. 11C shows the CPMG signal obtained with the prototype NMR receiver circuit as part of the experimental setup of FIG. 11A with the receive coil having an inductance of 4.1 µH.

FIG. 11C shows the CPMG signal obtained with the prototype NMR receiver circuit with the receive coil having an inductance $L_{coil}$ of 4.1 µH. The SNR is about 30% lower than results of the experiment of FIG. 11B. The bigger coil has approximately the same active volume, so the fact that SNR actually decreased suggests that the current noise of the prototype NMR receiver circuit increased sharply because of the larger source impedance as suggested by FIGS. 8A and 8B. The voltage gain of the prototype NMR receiver circuit is inversely proportional to the inductance $L_{coil}$ of the receive coil, so using the larger receive coil causes the voltage gain to decrease by a factor of 4.1/1.4=2.9. However, the output voltage only decreased by a factor of 1.2 as evident from FIG. 11C. This behavior implies that the larger receive coil produces an NMR signal that is 2.9/1.2=2.4 times larger than the smaller receive coil. This conclusion is not unreasonable considering that the larger coil has approximately double the number of turns, which results in a stronger RF field. However, using the larger receive coil caused the SNR to decrease by approximately 30%. This behavior implies that the larger source impedance caused the input-referred noise of the prototype NMR receiver circuit to increase by a factor of 2.3×1.3=3.1 at 2 MHz. This behavior is close to the theoretical predictions shown in FIGS. 8A and 8B. These observations suggest that an optimal coil size and geometry exists for maximizing SNR at a given Larmor frequency. Small coils will result in negligible current noise, but will also induce weak NMR signals. Large coils will induce larger signals, but suffer from increased current noise. The optimum will shift towards larger coils as the Larmor frequency decreases.

As described above, the transimpedance amplifier configuration of circuit 203 can be based on the LT6230-10 operational amplifier, which has an input stage that uses bipolar junction transistors (BJTs). The high transconductance of the BJT allows this design to have very low input-referred voltage noise (1.1 nV/Hz$^{1/2}$). However, the BJT also has a large base current, which creates high current noise (2.4 pA/Hz$^{1/2}$). Specifically, the LT6230-10 operational amplifier as well as other commercially-available low-noise, high-speed operational amplifiers suffer from a fundamental tradeoff between current noise and voltage noise. Such operational amplifiers utilize BJTs to realize the differential amplifier input stage because of the superior performance of the BJTs as compared to field-effect transistors (FETs). In order to reduce voltage noise, the BJTs of the differential amplifier input stage are operated at high bias current $I_C$, resulting in high input (base) current $I_B=I_C/\beta$, where $\beta$ is the current gain of the BJT transistor. Such high input base current results in high levels of current noise. The current noise can be largely eliminated by using FETs to realize the differential amplifier input stage. However, such FET-based designs for the differential amplifier input stage have reduced speed and significantly higher levels of voltage noise. As a result of the high current noise of the BJTs of the input stage of the operational amplifier, the total input-referred noise of the receiver circuitry increases rapidly with the impedance of the coil 102, i.e., with increasing frequency and/or coil inductance. This issue is exacerbated by the step-up transformer 201, which increases the effective impedance of the coil 102 by a factor of $n^2$, where n is the turn ratio of the step-up transformer 201. For the simulations of FIGS. 7, 8A and 8B and the prototype NMR receiver of FIGS. 11A, 11B, and 11C, the step-up transformer 201 is realized by the T36-1 transformer sold commercially by Mini-Circuits Laboratory of Brooklyn, N.Y. This results in high current noise that limits the usefulness of the receiver circuitry to coil impedances less than 12 Ohms, which is the impedance of a 4 µH coil at 500 KHz.

Figure 12:
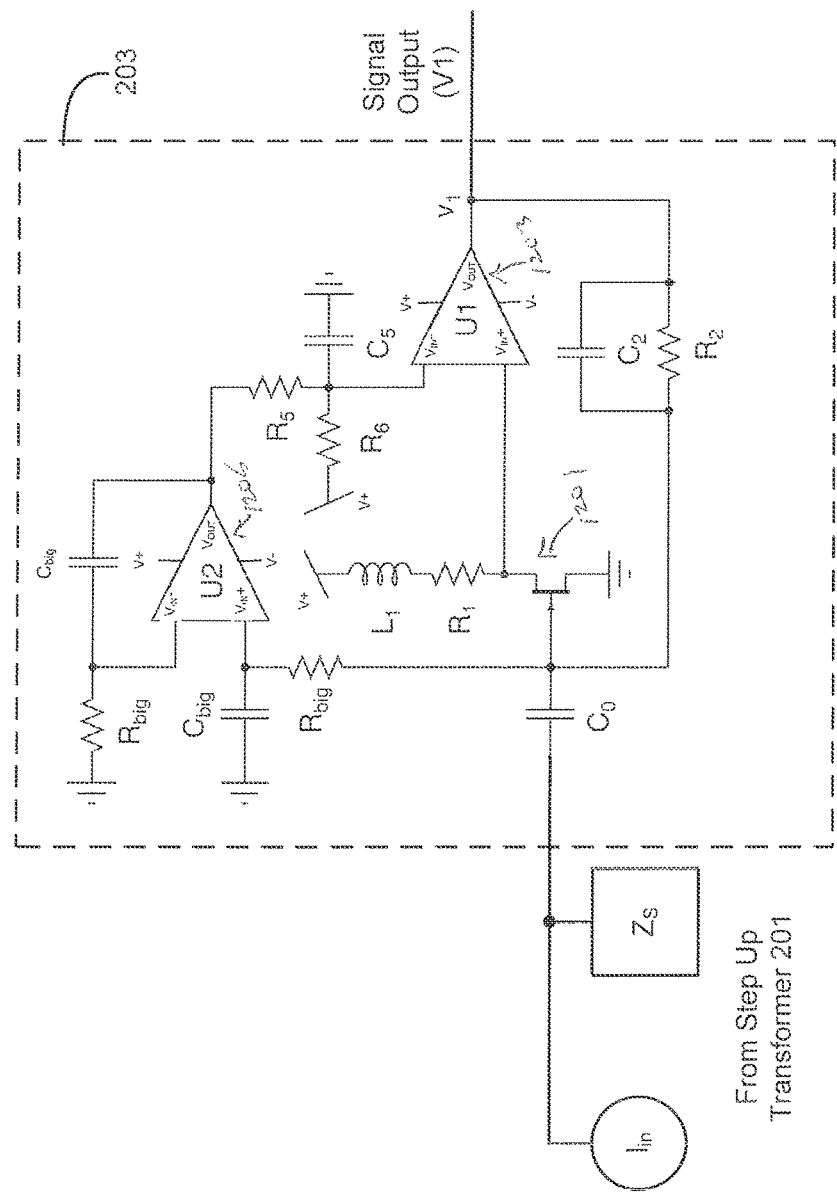
FIG. 12 is a schematic diagram illustrating an exemplary transimpedance amplifier circuit that can be used as part of preamplifier within an NMR receiver in accordance with one embodiment of the present disclosure.

In another embodiment shown in FIG. 12, the NMR receiver circuit 106 can include a TIA circuit 203' that uses a low-noise field-effect transistor (FET) 1201 at its input to reduce current noise, such as a junction field-effect transistor (JFET) or a metal-oxide field effect transistor (MOSFET). FETs are beneficial because they have lower current noise for the same voltage noise, in comparison to other types of transistors, such as bipolar junction transistors (BJT). As a result, the receiver will have a low noise figure, even when supporting a coil with a large inductance. At the same time, the TIA circuit 203' uses a low noise operational amplifier 1203 (such as the decompensated LT6230-10) to form a current-sense feedback loop to ensure large bandwidth. The TIA circuit 203' of FIG. 12 is similar to the TIA circuit 203 of FIG. 5 as previously described with the main difference being the addition of an input JFET 1201 and associated biasing circuitry. Specifically, the input JFET 1201 is a depletion mode device and its gate should be configured at DC ground in order to maximize transconductance and minimize input-referred voltage noise. This bias condition is ensured by configuring an operational amplifier 1205 to create a slow feedback loop that sets the gate of the input JFET 1201 at DC ground and sets the negative input terminal (Vin−) of the current-sensing operational amplifier 1203 at an appropriate value. The network formed by resistor R5, resistor R6 and capacitor C5 acts as a DC level shifter within this feedback loop. The input JFET 1201 is configured as a low-gain common-source stage with an inductor L1 and a resistor R1 coupled in series between the positive voltage supply (V+) and the drain of the input JFET 1201 as shown. The input JFET 1201 and the operational amplifier 1203 form a current sense loop with a feedback path that extends between the output terminal ($V_{OUT}$) of the operational amplifier 1203 and the gate of the input JFET 1201. This feedback path includes a resistor R2 and a compensation capacitor C2 coupled in parallel with respect to one another. Similar to the circuit of FIG. 5, the resistor R2 sets the gain of the circuit 203 and the compensation capacitor C2 reduces the voltage gain of the circuit 203 at high frequencies in order to ensure that it remains stable. The circuit 203 can also include a capacitor C0 coupled in series between the output of the step-up transformer 201 and the gate of the input JFET 1201 as shown in FIG. 12. This series-coupled capacitor C0 increases the source impedance of the step-up transformer 201 at low frequencies similar to the series-coupled capacitor C1 of the TIA circuit 203 of FIG. 5. The inductor L1 acts as a shunt-peaking element that increases the bandwidth of the common-source input JFET 1201 by adding a zero to the transfer function. The overall effect is to increase the stability (phase margin) of the current-sense loop formed by input JFET 1201 and the operational amplifier 1203. A large inductor (RF choke) and capacitor (not shown) can be coupled between the power supply (V+) and the inductor L1. The RF choke and capacitor can be configured to form an L-C low-pass filter having a desired cut-off frequency (such as approximately 1 kHz) that operates to remove unwanted high frequency noise of the power supply (V+) and thus improve the power supply rejection of the common-source input JFET 1201. The topology of the rest of the preamplifier of the NMR receiver circuit is unchanged from the design of FIG. 5. Specifically, the output of the TIA circuit 203' is passed to the differentiator circuit 205 of FIG. 5, and the output of the differentiator circuit 205 can be passed to the unitary gain circuit 207 as shown in FIG. 5. The frequency response of the TIA circuit 203' of FIG. 12 is that of an integrator (low-pass filter). The differentiator circuit 205 operates to compensate for the frequency response of the TIA circuit 203' and result in generally constant gain over the frequency range of interest similar to curves of FIG. 7. The unitary gain circuit 207 operates to provide a low-impedance output for driving long cables and/or the low input impedance of the spectrometer of the system.

For the common-source input JFET 1201 of the TIA circuit 203', the drain current $I_D$ and the small-signal transconductance $g_m$ in the saturation regime are given by:

$$I_D = \frac{\beta}{2}(V_{GS} - V_{T0})^2, \text{ and} \tag{21}$$

-continued $$g_m \equiv \frac{\delta I_D}{\delta V_{GS}} = \sqrt{2\beta I_D}. \quad (22)$$

To simplify the analysis, the analysis does not account for second-order effects like channel length modulation. Here, β is constant for a given transistor, and $V_{GS}$ and $V_{T0}$ are its gate-source and threshold voltages, respectively. The saturation condition is satisfied when $V_{DS} \geq (V_{GS} - V_{T0})$, where $V_{DS}$ is the drain-source voltage of the transistor. In the actual circuit of FIG. 12, the drain resistance $R_1$ must be small enough for this condition to be satisfied. Under these conditions, the input-referred voltage noise of the receiver circuitry can be estimated using a well-known formula for JFET thermal noise in the saturation regime. Specifically, the power spectral density (PSD) of the drain current noise is given by:

$$i_{no}^2 = \frac{8kTg_m}{3} + \frac{4kT}{R_1}. \quad (23)$$

The resultant output and input-referred voltage noise of the receiver circuitry are given by:

$$v_{no}^2 = i_{no}^2 R_1^2 = 4kTR_1\left(\frac{2}{3}g_m R_1 + 1\right) = 4kTR_1\left(\frac{2}{3}A_v + 1\right), \text{ and} \quad (24)$$

$$v_{ni}^2 = \frac{v_{no}^2}{A_v^2} \approx \frac{2}{3}\frac{4kTR_1}{A_v} = \frac{2}{3}\frac{4kT}{g_m} = \frac{2}{3}\frac{4kT}{\sqrt{2\beta I_D}}. \quad (25)$$

Here, $A_v \gg 1$ is the voltage gain of the input JFET 1201. In order to lower the input-referred voltage noise, the input JFET 1201 must provide a larger value of β (typically provided by a larger transistor), or the circuit can be configured to utilize a large value of $I_D$ and thus consume more power. Unfortunately transistor capacitances also increase with β, which reduces the bandwidth over which such low noise can be maintained. In particular, the following relationships are generally valid:

$$\beta \propto \mu \frac{W}{L},$$

$C_{gs} \propto WL$, $C_{gd} \propto WL$. JFET manufacturers usually specify the input-referred noise at zero gate bias, i.e., when $V_{GS}=0$. This situation results in above-threshold operation since most n-type JFETs have negative threshold voltages.

In one embodiment, the input JFET 1201 of FIG. 12 is the LSK170 device sold commerically by Linear Integrated Systems of Fremont, Calif. Advantageously, this device provides extremely low input-referred noise and moderate capacitance. Note that the current noise of JFETs is generally negligible unless the source resistance is very high. For example, the LSK170 has a noise-matching resistance of 100 KOhms for typical biasing conditions (e.g., $V_{GS}=0$). This value is approximately two orders of magnitude higher than bipolar transistors with similar input-referred voltage noise.

Figure 13:
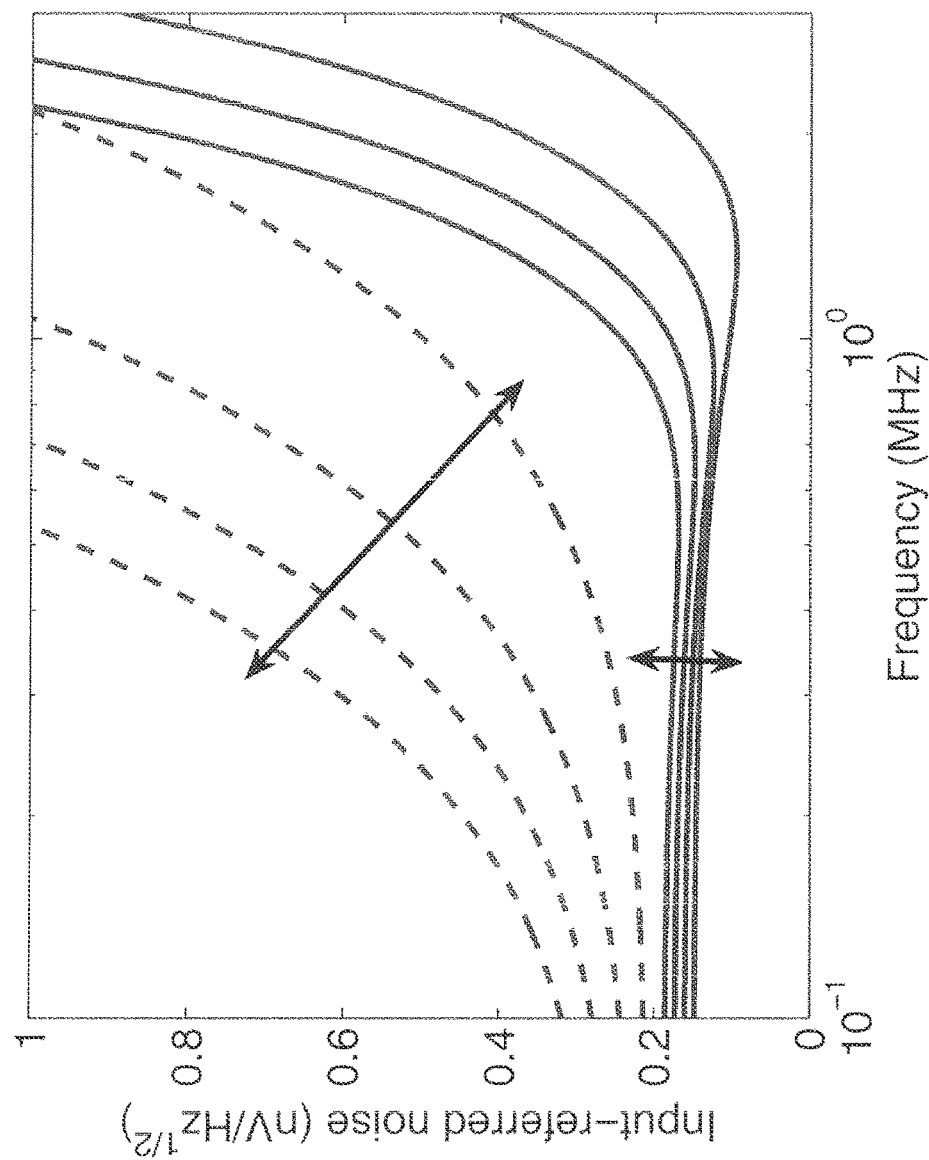
FIG. 13 shows the simulated input-referred noise power spectral density (PSD) for an NMR circuit employing a transimpedance amplifier circuit having a BJT-based input stage in accordance with the design of FIG. 5 (in dash lines) as well as the simulated input-referred noise PSD for an NMR circuit employing a transimpedance amplifier circuit having a JFET-based input stage in accordance with the design of FIG. 12 (in solid lines) for a number of coils of varying inductance.

The effects of reduced current noise can be seen in FIG. 13, which compares the simulated input-referred noise of the NMR receiver circuit that employs the BJT-based op-amp input stage of FIG. 4 (shown in dashed lines in FIG. 13) with the simulated input-referred noise of the NMR receiver circuit that employs the JFET-based input stage of FIG. 12 (shown in solid lines in FIG. 13) as a function of frequency and coil inductance. The simulated input-referred noise of the NMR receiver circuit that employs the JFET-based input stage (shown in solid lines in FIG. 13) is approximately 0.17 nV/Hz$^{1/2}$, which corresponds to a 1.7 Ohm resistor at 300 K at frequencies up to 1 MHz. This shows that the NMR receiver circuit that employs the JFET-based input stage has much lower noise than the NMR receiver circuit that employs the BJT-based op-amp input stage. The difference becomes more marked as the inductance of the receive coil increases, which results in higher source impedance and more current noise.

In one embodiment, an NMR receiver circuit that employs the JFET-based input stage of circuit 203' of FIG. 12 can have the following component values: capacitor C0 having a capacitance of 1.1 μF, the inductor L1 having an inductance of 47 μF, the resistor R1 having a resistance of 250 Ohms, the resistor R2 having a resistance of 200 KOhms, the compensation capacitor C2 having a capacitance of 1 pF, the capacitor $C_{big}$ having a capacitance of the 0.1 μF, the resistor $R_{big}$ having a resistance of 5 MOhms, the resistor R5 having a resistance of 10 KOhms, the resistor R6 having a resistance of 4.7 KOhms, the capacitor C5 having a capacitance of 1 μF, the capacitor C3 having a capacitance of 1 μF, the resistor R4 having a resistance of 750 Ohms, and the capacitor C4 having a capacitance of 50 pF. This NMR receiver circuit was measured to have a mid-band gain of 67 dB (2200 V/V) when connected to a 15 μH solenoid coil. This result is very close to simulations. The input-referred noise at 1 MHz was approximately 0.35 nV/Hz$^{1/2}$, which is equivalent to a 7.6 Ohm resistor at room temperature. This value is about a factor of two larger than simulation results; although, even with this noise level, the NMR receiver circuit is operational and the performance is good. It is also noted that the noise level above 2 MHz matches very well with simulations. This behavior indicates that the extra noise at 1 MHZ is likely produced by the input JFET 1201, which dominates the noise of the circuit at low frequencies, and not the op-amps or step-up transformer, which dominate at high frequencies. It therefore seems probable that the input JFET 1201 has higher noise levels than predicted by the simulation model. In fact, the data sheet for the LSK170 shows that the actual input-referred noise of this transistor can vary by over a factor of two (from 0.9 nV/Hz$^{1/2}$ to 1.9 nV/Hz$^{1/2}$), which is sufficient to explain the discrepancy between simulation results and measured results at 1 MHZ.

Figure 14:
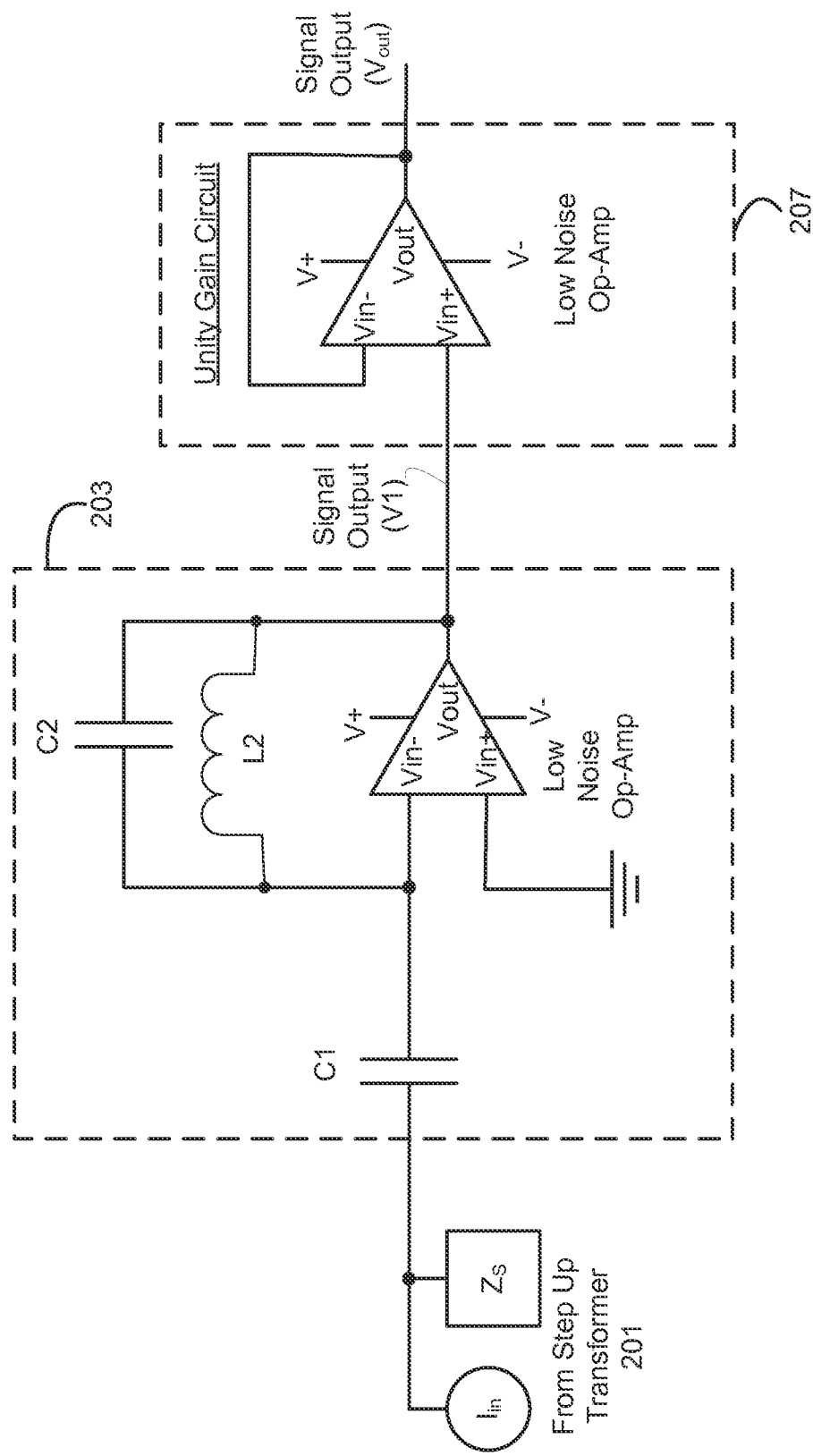
FIG. 14 is a schematic diagram illustrating another exemplary transimpedance amplifier circuit that can be used as part of preamplifier within an NMR receiver in accordance with one embodiment of the present disclosure.

FIG. 14 illustrates an additional embodiment of an NMR receiver circuit 106 with a step-up transformer 201 and a preamplifier 202 having a TIA circuit 203" that employs an inductor L2 in the feedback path between the output terminal ($V_{OUT}$) and the negative input terminal_($V_{IN}$) of the operational amplifier (such as the decompensated LT6230-10) to form a current-sense feedback loop to ensure large bandwidth. The TIA circuit 203" of FIG. 14 is similar to the TIA circuit 203 of FIG. 5 as previously described with the difference being the substitution of the inductor L2 for the resistive feedback element R2. In this case, the inductor L2 can be configured such that the TIA circuit 203" provides a generally constant voltage gain with frequency over the frequency band of interest similar to combination of the TIA circuit 203 and the differentiator circuit 205 of FIG. 5 as shown in FIG. 7. In this case, the differentiator circuit 205 can be omitted from the preamplifier 202. The optional unitary gain circuit 207 can be coupled to the output of the TIA circuit 203" to provide for low output impedance, if desired.

Figure 15:
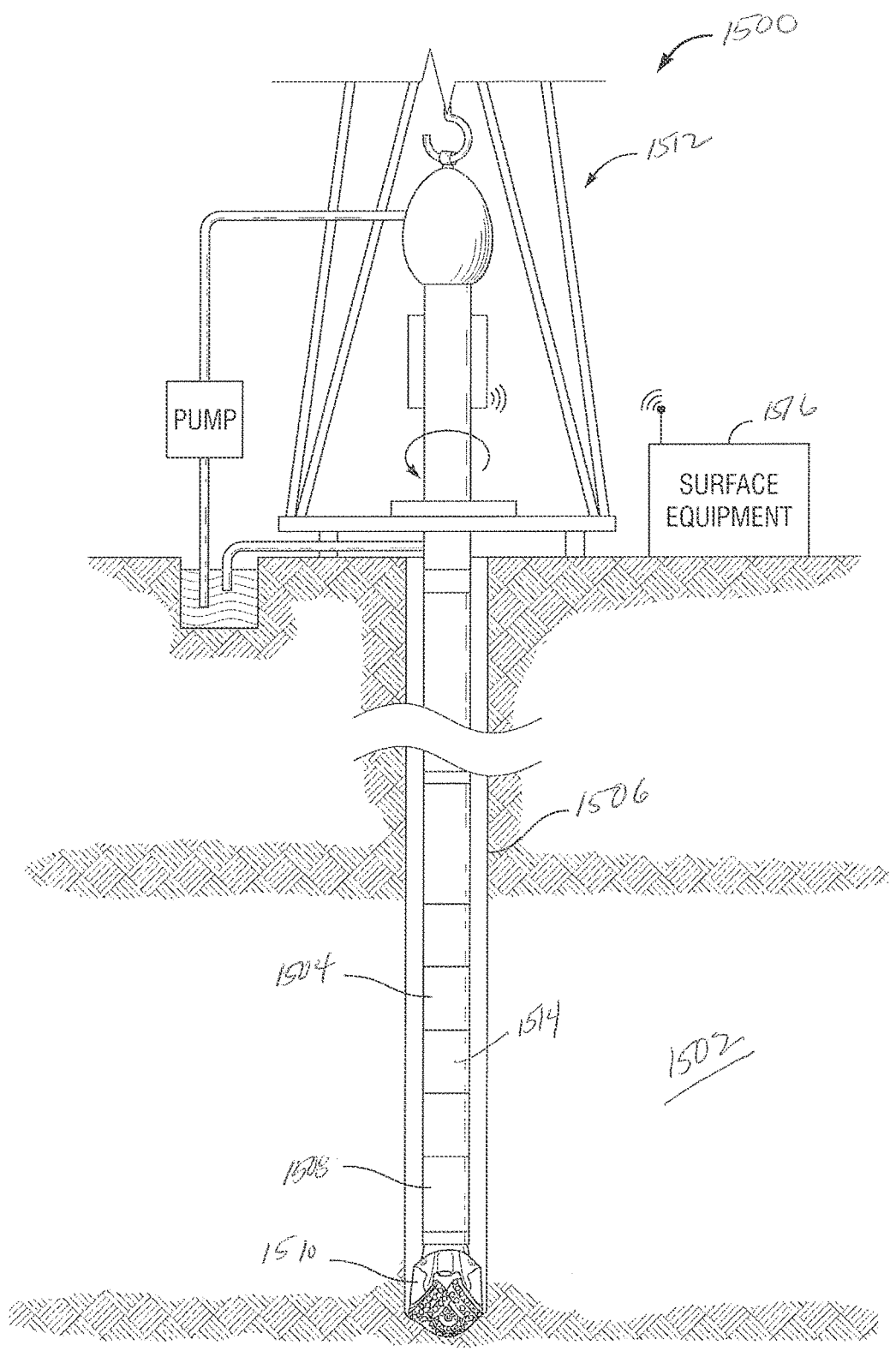
FIG. 15 shows a logging-while-drilling (LWD) system in accordance with one embodiment of the present disclosure.
Figure 16:
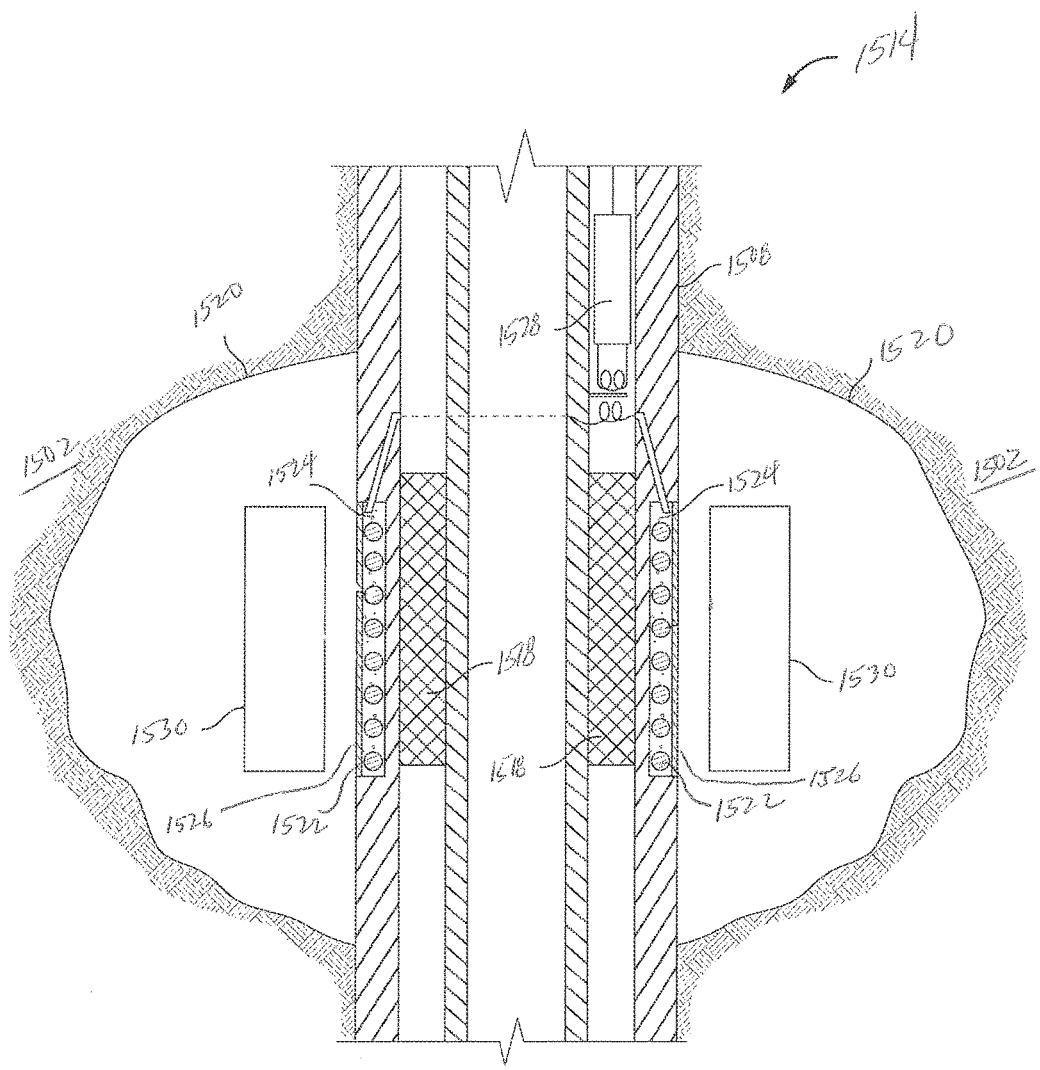
FIG. 16 shows a LWD NMR logging module in accordance with one embodiment of the present disclosure.

FIGS. 15 and 16 show an embodiment of the present disclosure directed to oil and gas field applications, such as wellbore logging tools. In particular, FIG. 15 shows a logging-while-drilling (LWD) system 1500 for investigating an earth formation 1502 and determining one or more properties of the formation 1502, while a drilling operation is performed. The LWD system 1500 includes a drill string 1504. The drill string 1504 is disposed within a wellbore 1506 that traverses the formation 1502. The drill string 1504 includes a drill collar 1508 with a drill bit 1510 disposed at the lower-end of the drill collar 1508. The LWD system 1500 also includes a surface system with a derrick assembly and platform assembly 1512 positioned over the wellbore 1506. The derrick assembly 1512 rotates the drill string 1504 and, as the drill string rotates, the drill bit 1510 drills deeper into the wellbore 1506. An LWD NMR logging module 1514 is disposed within the drill collar 1508 so that the module can log the surrounding earth formation as the drilling operation is performed. The NMR logging module 1514 communicates with surface equipment 1516, which includes an operator interface for communicating with the module. Such an operator interface has already been described with reference to FIG. 1. In various embodiments, the NMR logging module 1514 and operator interface can communicate via any one of a wired-drill pipe connection, an acoustic telemetry connection, optical communication, and/or electronic communication.

FIG. 16 shows details of the NMR logging module 1514 of FIG. 15. The NMR logging module 1514 is configured to apply NMR pulse sequences to the formation. The NMR logging module 1514 includes magnet sections 1518 that generate a static magnetic field within a zone of sensitivity 1520 within the formation 1502. The NMR logging module 1514 also includes a coil 1522 is disposed within an axial slot 1524 of the drill collar 1508. The slot 1524 is filled with an insulator, such as ceramic, epoxy, or fiberglass. As explained above, the coil 1522 is wound around the drill collar 1508 within the slot 1524. The slot 1524 is sealed using a cover 1526. In some embodiments, the cover 1526 is formed from a non-magnetic material and/or non-conductive material. At one end, the coils sections are grounded (e.g., to the drill collar 1508). At the other end, the coil sections are coupled to NMR electronics 1528, which are part of the NMR logging module 1514. The NMR electronics 1528 include an NMR transmitter 104 and an NMR receiver 106. The NMR receiver 106 includes a transformer and a preamplifier with a transimpedance amplifier circuit, such as any of the NMR receivers 106 described in FIGS. 1-14. The NMR electronics 1528 are coupled to the coil 1522 via, for example, pressure feed-throughs. The NMR electronics 1528 supplies a time-varying RF signal to the coil 1522 such that coil 1522 applies an oscillating magnetic field (e.g., NMR pulse sequences) to an area of interest 1530 within the zone of sensitivity 1520 within the formation 1502. In some embodiments, the oscillating magnetic field is axially symmetric to facilitate measurements during rotation of the drill string. Further details of NMR LWD systems are described in U.S. Pat. No. 5,629,623 issued on May 13, 1997 and U.S. Pat. No. 6,392,410, issued on May 21, 2002. Each of these patents is incorporated by reference herein in their entireties. One specific example of a NMR LWD tool is Schlumberger's proVISION™ tool.

The NMR receivers and methods described herein are not limited to any particular device type or system. The NMR receivers and methods described herein can be implemented in surface environments, such as in a laboratory. The NMR transmitters can be used in chemical production, food production, material inspection, and infrastructure inspection (e.g., building and bridges).

The NMR receivers and methods described herein are not limited to any particular wellbore application. The NMR systems and methods described herein can be used with LWD systems, such as the one shown in FIGS. 15 and 16. Also, the NMR systems and methods described herein can be applied to wireline systems (e.g., a wireline tool) or measuring-while-drilling systems (e.g., MWD tools). Illustrative embodiments can also be used with any suitable means of conveyance, such as armored cable or coiled tubing. Furthermore, the NMR receivers and methods described herein can be used to investigate a substance within an earth formation outside the wellbore tool (e.g., outside the coil) or to investigate a substance within a flow line or chamber within a wellbore tool (e.g., inside the coil).

The NMR systems and methods described herein are not limited to implementing NMR techniques and sequences. The systems and devices described herein can also be used to implement other magnetic resonance (MR) techniques and sequences, such as nuclear quadrupole resonance (NQR) techniques and sequences.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

We claim:

1. A magnetic resonance (MR) receiver for processing MR signals, the receiver comprising:
   a transformer configured to amplify the MR signals; and
   a preamplifier configured to receive the MR signals from the transformer, wherein the preamplifier comprises a transimpedance amplifier circuit with an input stage that includes a field effect transistor.

2. The receiver of claim 1, wherein the preamplifier further comprises a differentiator circuit.

3. The receiver of claim 2, wherein the transimpedance amplifier circuit is configured to convert an input signal, which is proportional to current flowing from an NMR coil to the transformer, to an output signal in accordance with a defined transimpedance gain, and wherein voltage gain of the transimpedance amplifier circuit decreases with frequency over a frequency band of interest.

4. The receiver of claim 3, wherein the differentiator circuit is configured to process the output signal produced by the transimpedance amplifier circuit with voltage gain, wherein the voltage gain of the differentiator circuit increases with frequency over the frequency band of interest such that the resultant signal produced by the differentiator circuit has a voltage gain with respect to the input signal that is generally constant with frequency over the frequency band of interest.

5. The receiver of claim 1, wherein the transimpedance amplifier circuit comprises an operational amplifier.

6. The receiver of claim 5, wherein the transimpedance amplifier circuit comprises
   a decompensated operational amplifier having a pair of input terminals and an output terminal; and
   a feedback path coupled between the output terminal and one input terminal of the decompensated operational amplifier, wherein the feedback path includes a compensation capacitor external to the decompensated operational amplifier.

7. The receiver of claim 6, wherein the feedback path further comprises a resistor coupled in parallel with the compensation capacitor, wherein the resistor provides an electrical resistance that dictates the voltage gain of the transimpedance amplifier circuit.

8. The receiver of claim 1, wherein the transimpedance amplifier circuit comprises a series-coupled capacitor at its input which operates to filter out unwanted low frequency components of the input current signal.

9. The receiver of claim 1, wherein the transimpedance amplifier circuit comprises:
   a first operational amplifier having a pair of input terminals and an output terminal, wherein the field effect transistor is operably coupled to one input terminal of the first operational amplifier; and
   a feedback path coupled between the output terminal of the first operational amplifier and a gate of the field effect transistor.

10. The receiver of claim 9, wherein the first operational amplifier is a decompensated operational amplifier and the feedback path comprises a compensation capacitor external to the decompensated operational amplifier.

11. The receiver of claim 10, wherein the feedback path further comprises a resistor coupled in parallel with the compensation capacitor, wherein the resistor provides an electrical resistance that dictates the voltage gain of the transimpedance amplifier circuit.

12. The receiver of claim 9, wherein the field effect transistor of the input stage is configured as a common-source stage with a resistor coupled in series between a positive voltage supply and the drain of the field effect transistor.

13. The receiver of claim 12, wherein the input stage further includes an inductor coupled in series with the resistor between the positive voltage supply and the drain of the field effect transistor.

14. The receiver of claim 9, wherein the transimpedance amplifier circuit further comprises biasing circuitry for biasing the gate of the field effect transistor.

15. The receiver of claim 14, wherein the biasing circuitry comprises:
   a second operational amplifier with a pair of input terminals and an output terminal;
   a resistive network coupled between a power supply source, the first operational amplifier, and the output terminal of the second operational amplifier; and
   a resistor coupled between the gate of the field effect transistor and one of the input terminals of the second operational amplifier.

16. The receiver of claim 1, wherein the frequency band of interest lies within the frequency range between 50 KHz and 10 MHz.

17. The receiver of claim 1, wherein the receiver is part of a wellbore tool.

18. The receiver of claim 1, wherein the field effect transistor is a junction field effect transistor.

19. A magnetic resonance (MR) receiver for processing MR signals, the receiver comprising:
   a transformer configured to amplify the MR signals; and
   a preamplifier configured to receive the MR signals from the transformer, wherein the preamplifier includes a transimpedance amplifier circuit configured to convert an input signal, which is proportional to current flowing from an NMR coil to the transformer, to an output signal in accordance with a defined transimpedance gain and the transimpedance amplifier circuit comprises:
      an operational amplifier circuit having a pair of input terminals and an output terminal; and
      a feedback path coupled between the output terminal and one input terminal of the operational amplifier, wherein the feedback path includes an inductor configured such that the resultant signal produced by the transimpedance amplifier circuit has a voltage gain with respect to the input signal that is generally constant with frequency over a frequency band of interest.

20. The receiver of claim 19, wherein the operational amplifier is a decompensated operational amplifier and the feedback path includes a compensation capacitor external to the decompensated operational amplifier.

21. The receiver of claim 19, wherein the frequency band of interest lies within the frequency range between 50 KHz and 10 MHz.

22. The receiver of claim 19, wherein the receiver is part of a wellbore tool.

23. A method for processing a magnetic resonance (MR) signal, the method comprising:
   receiving the MR signal;
   amplifying the MR signal using a transformer;
   passing the MR signal produced by the transformer to a transimpedance amplifier circuit comprising an input stage with a field effect transistor; and
   passing the MR signal produced by the transimpedance amplifier circuit to a differentiator circuit for further amplification.

24. The method of claim 23, further comprising:
   performing the method in a wellbore.

* * * * *